US007863451B2

(12) United States Patent
Muller et al.

(10) Patent No.: US 7,863,451 B2
(45) Date of Patent: Jan. 4, 2011

(54) PROCESSES FOR THE PREPARATION OF SUBSTITUTED 2-(2,6-DIOXOPIPERIDIN-3-YL)-1-OXOISOINDOLINES

(75) Inventors: George W. Muller, Bridgewater, NJ (US); Roger Chen, Edison, NJ (US); Manohar Tukaram Saindane, Monmouth Junction, NJ (US); Chuansheng Ge, Belle Mead, NJ (US)

(73) Assignee: Celgene Corporation, Summit, NJ (US)

( * ) Notice: Subject to any disclaimer, the term of this patent is extended or adjusted under 35 U.S.C. 154(b) by 912 days.

(21) Appl. No.: 11/219,589

(22) Filed: Sep. 1, 2005

(65) Prior Publication Data
US 2006/0052609 A1   Mar. 9, 2006

Related U.S. Application Data

(60) Provisional application No. 60/607,409, filed on Sep. 3, 2004.

(51) Int. Cl.
*C07D 403/04* (2006.01)
(52) U.S. Cl. ...................................... 546/201
(58) Field of Classification Search ................. 546/201
See application file for complete search history.

(56) References Cited

U.S. PATENT DOCUMENTS

| 5,134,127 | A | 7/1992 | Stella et al. | |
| 5,463,063 | A | 10/1995 | Muller | 546/201 |
| 5,635,517 | A | 6/1997 | Muller et al. | |
| 5,698,579 | A | 12/1997 | Muller | |
| 5,798,368 | A | 8/1998 | Muller et al. | |
| 5,874,448 | A | 2/1999 | Muller et al. | |
| 5,877,200 | A | 3/1999 | Muller | |
| 5,929,117 | A | 7/1999 | Muller et al. | |
| 5,955,476 | A | 9/1999 | Muller et al. | |
| 6,114,355 | A | 9/2000 | Buerger et al. | |
| 6,235,756 | B1 | 5/2001 | D'Amato | |
| 6,281,230 | B1 | 8/2001 | Muller et al. | |
| 6,316,471 | B1 | 11/2001 | Muller et al. | |
| 6,335,349 | B1 | 1/2002 | Muller et al. | |
| 6,380,239 | B1 | 4/2002 | Muller et al. | |
| 6,395,754 | B1 | 5/2002 | Muller et al. | |
| 6,403,613 | B1 | 6/2002 | Man et al. | |
| 6,458,810 | B1 | 10/2002 | Muller et al. | |
| 6,476,052 | B1 | 11/2002 | Muller et al. | |
| 6,555,554 | B2 | 4/2003 | Muller et al. | |
| 7,091,343 | B2 | 8/2006 | Bebbington et al. | 544/238 |
| 7,153,867 | B2 * | 12/2006 | Shah et al. | 514/323 |
| 7,153,876 | B2 * | 12/2006 | Schudok et al. | 514/345 |
| 2002/0045643 | A1 | 4/2002 | Muller et al. | |
| 2003/0045552 | A1 | 3/2003 | Robarge et al. | |
| 2003/0096841 | A1 | 5/2003 | Robarge et al. | |
| 2004/0029832 | A1 | 2/2004 | Zeldis | |
| 2004/0087546 | A1 | 5/2004 | Zeldis | |
| 2004/0091455 | A1 | 5/2004 | Zeldis | |
| 2004/0147558 | A1 | 7/2004 | Treston et al. | 514/323 |
| 2004/0220144 | A1 | 11/2004 | Zeldis | |
| 2007/0004920 | A1 | 1/2007 | Ge et al. | 546/200 |
| 2007/0049618 | A1 | 3/2007 | Muller et al. | 514/323 |
| 2008/0214615 | A1 | 9/2008 | Muller et al. | 514/323 |

FOREIGN PATENT DOCUMENTS

| WO | WO 95/01348 | 1/1995 |
| WO | WO 98/03502 | 1/1998 |
| WO | WO 98/54170 | 12/1998 |
| WO | WO 00/55134 | 9/2000 |
| WO | WO 02/059106 | 8/2002 |
| WO | WO 2005/005409 | 1/2005 |
| WO | WO 2009/111948 | 9/2009 |
| WO | WO 2009/114601 | 9/2009 |

OTHER PUBLICATIONS

Exahibit I.*
Braga et al. "making crystals . . ." Chem. Commun. p. 3635-3645 (2005).*
Katsura et al. "Preparation of . . ." CA 133:237671 (2000).*
Soederberg et al. "Synthesis of . . ." CA 141:314104 (2003).*
Exhibit I.*
Morrison &Boyd "Organic Chemistry" p. 680-681 (1073).*
Muller et al. "2-(2,6-dioxopiperidin-3-yl . . . " CA152:37403 (2009).*
"acid chloride to amide" Internet p. 1-3 (2010).*
Capitosti et al., Facile synthesis of an azido-labeled thalidomide analogue. Org Lett. Aug. 7, 2003;5(16):2865-7.
Chang et al., A synthesis of racemic thalidomide. Synthetic Communications, 2003, 33(8):1375-1382.
Eger et al., Synthesis, Central nervous system activity and teratogenicity of a homothalidomide. Arzneimittelforschung. Oct. 1990;40(10):1073-5.
Gutschow et al., Aza analogues of thalidomide: synthesis and evaluation as inhibitors of tumor necrosis factor-alpha production in vitro. Bioorg Med Chem. Apr. 2001;9(4):1059-65.
He te al., Synthesis of thalidomide analogs and their biological potential for treatment of great-versus-host disease (GVHD). Abstracts of papers of the American Chemical Society 206:216-MEDI, Aug. 22, 1993.
Hess et al., Synthesis and immunological activity of water-soluble thalidomide prodrugs. Bioorg Med Chem. May 2001 ;9(5):1279-91.
Klinsberg, Erwin. *Chemistry of Heterocyclic Compounds*. New York: Wiley & Sons, 1960 (pp. 295-296).

(Continued)

*Primary Examiner*—Celia Chang
(74) *Attorney, Agent, or Firm*—Jones Day

(57) ABSTRACT

The present invention concerns new processes for the preparation of substituted 2-(2,6-dioxopiperidin-3-yl)-1-oxoisoindolines which are useful for preventing or treating diseases or conditions related to an abnormally high level or activity of TNFα. The invention provides processes for the commercial production of substituted 2-(2,6-dioxopiperidin-3-yl)-1-oxoisoindolines including, but not limited to, the therapeutically active 3-(4-amino-1-oxoisoindolin-2-yl)piperidine-2,6-dione.

55 Claims, No Drawings

OTHER PUBLICATIONS

Lima et al., Synthesis and anti-inflammatory activity of phthalimide derivatives, designed as new thalidomide analogues. Bioorg Med Chem. Sep. 2002;10(9):3067-73.

Luzzio et al., Synthesis of racemic cis-5-hydroxy-3-phthalimidoglutarimide. A metabolite of thalidomide isolated from human plasma. J Org Chem. Nov. 25, 2005;70(24):10117-20.

Luzzio et al., Thalidomide metabolites and analogs. Part 2: Cyclic derivatives of 2-N-phthalimido-2S,3S(3-hydroxy) ornithine. Tetrahedron Lett. 2000, 41:7151-55.

Luzzio et al., Thalidomide metabolites and analogues. 3. Synthesis and antiangiogenic activity of the teratogenic and TNF alpha-modulatory thalidomide analogue 2-(2,6-dioxopiperidine-3-yl)phthalimidine. J Med Chem. Aug. 28, 2003;46(18):3793-9.

Luzzio et al., Thalidomide metabolites. Part 1: Derivatives of (+)-2-(N-phthalimido)-γ-hydroxyglutamic acid. Tetrahedron Letters, 2000, 41:2275-2278.

Luzzio et al., Thalidomide analogues: derivatives of an orphan drug with diverse biological activity. Expert Opin. Ther. Patents, 2004, 14(2):215-229.

Machado et al., Design, synthesis and antiinflammatory activity of novel phthalimide derivatives, structurally related to thalidomide. Bioorg Med Chem Lett. Feb. 15, 2005;15(4):1 169-72.

Man et al., Alpha-fluoro-substituted thalidomide analogues. Bioorg Med Chem Lett. Oct. 20, 2003;13(20):3415-7.

Muller et al., A concise two-step synthesis of thalidomide. Organic Process Research & Development. 1999, 3:139-140.

Muller et al., Structural modifications of thalidomide produce analogs with enhanced tumor necrosis factor inhibitory activity. J Med Chem. Aug. 16, 1996;39(17):3238-40.

Noguchi et al., Angiogenesis inhibitors derived from thalidomide. Bioorg Med Chem Lett. Dec. 15, 2005;15(24):5509-13.

Pablo Mureil M et al., Synthesis and pharmacological evaluation of a thalidomide analog, the 3-phthalimide-3-(3,4- dimethoxyphenyl)-propanioc acid in liver cirrhosis induced by bile duct ligation in the rat. Hepatology, 2001, 34(4):pp517A, Abastract#1379.

Park et al., Synthesis and structure-activity relationships of novel compounds for the inhibition of TNF-alpha production. Arch Pharm Res. Aug. 2000;23(4):332-7.

Shah et al., Synthesis and enantiomeric separation of 2-phthalimidino-glutaric acid analogues: potent inhibitors of tumor metastasis. J Med Chem. Aug. 12, 1999;42(16):3014-7.

U.S. Appl. No. 10/693,794, filed Oct. 23, 2003, Zeldis.
U.S. Appl. No. 10/900,270, filed Jul. 28, 2004, Muller et al.
U.S. Appl. No. 10/900,332, filed Jul. 28, 2004, Muller et al.
U.S. Appl. No. 10/934,863, filed Sep. 3, 2004, Jaworsky et al.
U.S. Appl. No. 60/499,723, filed Sep. 4, 2003, Jaworsky.
U.S. Appl. No. 60/518,600, filed Nov. 6, 2003, Zeldis.
U.S. Appl. No. 60/554,923, filed Mar. 22, 2004, Zeldis et al.

Corral et al., 1999, "Immunomodulation by thalidomide and thalidomide analogues," Ann. Rheum. Dis. 58(Suppl. 1):1107-113.

Dezube et al., 1990, "Pentoxifylline and wellbeing in patients with cancer," Lancet 335(8690):662.

Glogau, 2000, "The risk of progression to invasive disease," J. Am. Acad. Dermatol. 42(1 Pt 2):23-24.

Goette, 1981, "Topical chemotherapy with 5-fluorouracil. A review," J. Am. Acad. Dermatol. 4(6):633-649.

He et al., 1993, "Synthesis of thalidomie analogs and their biological potential for treatment of graft versus host diseases," 206th American Chemical Society, Chicago, IL, Med. Chem. paper 216.

Hinshaw et al., 1990, "Survival of primates in LD100 septic shock following therapy with antibody to tumor necrosis factor (TNF alpha)," Circ. Shock. 30(3):279-92.

Jonsson et al., 1972, "Chemical structure and teratogenic properties: 3. A review of available data on structure-activity relationships and mechanism of action of thalidomide analogs," Acta. Pharm. Suecica 9:521-542.

Marks et al., 1988, "Malignant transformation of solar keratoses to squamous cell carcinoma," Lancet 1(8589):795-797.

Millar et al., 1989, "Tumour necrosis factor in bronchopulmonary secretions of patients with adult respiratory distress syndrome," Lancet 2(8665):712-4.

Muller et al., 1996, "Structural modifications of thalidomide produce analogs with enhanced tumor necrosis factor inhibitory activity," J. Med. Chem. 39(17):3238-3240.

Muller et al., 1998, "Thalidomide analogs and PDE4 inhibition," Bioorg. Med. Chem. Lett. 8(19):2669-2674.

Muller et al., 1999, "Amino-substituted thalidomide analogs: Potent inhibitors of TNF-☐production," Bioorg. Med. Chem. Lett. 9:1625-1630.

Tracey et al., 1987, "Anti-cachectin/TNF monoclonal antibodies prevent septic shock during lethal bacteraemia," Nature 330(6149):662-4.

Lachman et al., *The Theory and Practice of Industrial Pharmacy (3rd edition)*, Lee & Febiger, Philadelphia (1986), pp. 681 and 756.

Varala and Adapa, 2005, "A Practical and Efficient Synthesis of Thalidomidevia Na/Liquid $NH_3$ Methodology," *Organic Process Research and Development* 9:853-856.

Xiao et al., Solid-phase synthesis of thalidomide and its analogues. J Comb Chem. Mar. 2002-Apr. 2002;4(2):149-53.

* cited by examiner

PROCESSES FOR THE PREPARATION OF SUBSTITUTED 2-(2,6-DIOXOPIPERIDIN-3-YL)-1-OXOISOINDOLINES

This application claims the benefit of U.S. provisional application No. 60/607,409, filed Sep. 3, 2004, the contents of which are incorporated by reference herein in their entirety.

1. FIELD OF THE INVENTION

The present invention relates to processes for the preparation of compounds useful for reducing levels or activity of tumor necrosis factor α in a mammal. More specifically, the invention relates to processes for the synthesis of substituted 2-(2,6-dioxopiperidin-3-yl)-1-oxoisoindolines. In particular, the invention relates to processes useful for the preparation of 3-(4-amino-1-oxoisoindolin-2-yl)-piperidine-2,6-dione.

2. BACKGROUND OF THE INVENTION

Excessive or unregulated production of tumor necrosis factor α, or TNFα, has been implicated in a number of disease conditions. These include endotoxemia and/or toxic shock syndrome (Tracey et al., *Nature* 330, 662-664 (1987) and Hinshaw et al., *Circ. Shock* 30, 279-292 (1990)), cachexia (Dezube et al., *Lancet* 335 (8690), 662 (1990)), and Adult Respiratory Distress Syndrome (Millar et al., *Lancet* 2 (8665), 712-714 (1989)). Certain substituted 2-(2,6-dioxopiperidin-3-yl)-1-oxoisoindolines have been shown to reduce levels of TNFα (International Publication No. WO 98/03502, incorporated herein by reference in its entirety).

An oxoisoindoline that has demonstrated particular therapeutic promise is 3-(4-amino-1-oxoisoindolin-2-yl)-piperidine-2,6-dione (REVLIMID™). This compound has been shown to be useful in treating and preventing a wide range of diseases and conditions including, but not limited to, inflammatory diseases, autoimmune diseases, and cancers including both solid and homological cancers. REVLIMID has received Fast Track Designation from the Food and Drug Administration for the treatment of multiple myeloma and myelodysplastic syndromes. Furthermore, REVLIMID is in late-stage clinical trials for the treatment of hematological and solid tumor cancers and immunological and inflammatory diseases.

Existing methods for synthesizing substituted 2-(2,6-dioxopiperidin-3-yl)-1-oxoisoindolines are described in International Publication No. WO 98/03502 (See page 7, line 22, to page 10, line 33, and Examples 1 to 18) and Muller et al., *Bioorgan. Med. Chem. Lett.* 9, 1625-1630 (1999). In one existing method, an N-protected glutamine is cyclized and then deprotected to generate an α-aminoglutarimide hydrochloride. The α-aminoglutarimide hydrochloride is coupled to a substituted methyl 2-bromomethylbenzoate to form a 2-(2,6-dioxopiperidin-3-yl)-1-oxoisoindoline. A benzo substituent can then be transformed to another substituent if desired.

While these methods are enabling and useful for preparing substituted 2-(2,6-dioxopiperidin-3-yl)-1-oxoisoindolines, there are possibilities for alterations that may result in a more efficient synthesis.

Citation of any reference in Section 2 of this application is not to be construed as an admission that such reference is prior art to the present application.

3. SUMMARY OF THE INVENTION

The present invention provides processes for the commercial production of substituted 2-(2,6-dioxopiperidin-3-yl)-1-oxoisoindolines that are cost effective and readily scaleable with commercial reagents. In one embodiment, the invention provides a process for preparing a substituted 2-(2,6-dioxopiperidin-3-yl)-1-oxoisoindoline comprising the steps of: (1) esterifying an N-protected or -unprotected glutamine; (2) deprotecting the α-amino group of the esterified glutamine if it is protected; (3) coupling the N-deprotected, esterified glutamine with an optionally substituted 2-haloalklylbenzoate; (4) cyclizing the coupled product; and (5) optionally transforming one or more benzo substituents on the cyclized product into other substituent(s) in one or more steps.

In another embodiment, the invention provides a process for preparing a substituted 2-(2,6-dioxopiperidin-3-yl)-1-oxoisoindoline comprising the steps of: (1) esterifying an N-protected or -unprotected glutamine; (2) deprotecting the α-amino group of the esterified glutamine if it is protected; (3) coupling the N-deprotected, esterified glutamine with an optionally substituted 2-haloalklylbenzoate; (4) transforming one or more benzo substituents on the coupled product into other substituent(s) in one or more steps; and (5) cyclizing the transformed product.

In yet other embodiments, the present invention provides processes for preparing substituted 2-(2,6-dioxopiperidin-3-yl)-1-oxoisoindolines as set forth in Scheme 1, wherein: $R^1$-$R^9$, X, and $ProtG^1$ are as described below. $R^{1'}$-$R^{4'}$ denote that one or more of the $R^1$-$R^4$ substituents may optionally be transformed to the corresponding $R^{1'}$-$R^{4'}$ substituents, respectively, in one or more steps. One of these embodiments comprises steps 1, 2, 3, 4, and 5. Another embodiment comprises steps 1, 2, 3, 6, and 7.

In still other embodiments, the invention provides processes for preparing mono-benzo-substituted 2-(2,6-dioxopiperidin-3-yl)-1-oxoisoindolines as set forth in Scheme 2, wherein $R^1$-$R^9$, X, and $ProtG^1$ are as described below. The benzo substituent $R^1$ may be converted into $R^2$ if desired. One of these embodiments comprises steps 1, 2, 3, 4, and 5. Another embodiment comprises steps 1, 2, 3, 6, and 7.

In yet other embodiments, the invention provides processes for synthesizing 3-(4-amino-1-oxoisoindolin-2-yl)-piperidine-2,6-dione as set forth in Scheme 3. One of these embodiments comprises steps 1, 2, 3, 4, and 5. Another embodiment comprises steps 1, 2, 3, 6, and 7.

In still another embodiment, the processes of the present invention are useful for preparing substituted 2-(2,6-dioxopiperidin-3-yl)-1-oxoisoindolines or pharmaceutically acceptable salts, hydrates, solvates, or polymorphs thereof. In yet another embodiment, the processes of the invention are useful for preparing compounds useful for preventing or treating diseases or conditions related to an abnormally high level or activity of TNFα. In yet another embodiment, the processes of the invention are useful for preparing compounds useful for treating or preventing oncological conditions.

4. DETAILED DESCRIPTION OF THE INVENTION

4.1 Terminology

As used herein and unless otherwise indicated, the term "halo", "halogen", or the like means —F, —Cl, —Br, or —I.

As used herein and unless otherwise indicated, the term "lower molecular weight halo" means —F or —Cl.

As used herein and unless otherwise indicated, the term "higher molecular weight halo" means —Br or —I.

As used herein and unless otherwise indicated, the term "alkyl" means a saturated, monovalent, unbranched or branched hydrocarbon chain. Examples of alkyl groups include, but are not limited to, $(C_1-C_6)$alkyl groups, such as methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, and hexyl. Longer alkyl groups include heptyl, octyl, nonyl and decyl groups. An alkyl group can be unsubstituted or substituted with one or more suitable substituents.

As used herein and unless otherwise indicated, the term "alkoxy" means an alkyl group that is linked to another group via an oxygen atom (i.e., —O-alkyl). An alkoxy group can be unsubstituted or substituted with one or more suitable substituents. Examples of alkoxy groups include, but are not limited to, $(C_1-C_6)$alkoxy groups, such as —O-methyl, —O-ethyl, —O-propyl, —O-isopropyl, —O-2-methyl-1-propyl, —O-2-methyl-2-propyl, —O-2-methyl-1-butyl, —O-3-methyl-1-butyl, —O-2-methyl-3-butyl, —O-2,2-dimethyl-1-propyl, —O-2-methyl-1-pentyl, 3-O-methyl-1-pentyl, —O-4-methyl-1-pentyl, —O-2-methyl-2-pentyl, —O-3-methyl-2-pentyl, —O-4-methyl-2-pentyl, —O-2,2-dimethyl-1-butyl, —O-3,3-dimethyl-1-butyl, —O-2-ethyl-1-butyl, —O-butyl, —O-isobutyl, —O-t-butyl, —O-pentyl, —O-isopentyl, —O-neopentyl and —O-hexyl.

As used herein and unless otherwise indicated, the term "lower alkyl" means alkyl having from 1 to 4 carbon atoms. Examples include, but are not limited to, methyl, ethyl, propyl, isopropyl, isobutyl, and tertiary butyl ($^t$Bu, or t-butyl).

As used herein and unless otherwise indicated, the term "lower alkoxy" means a lower alkyl group that is linked to another group via an oxygen atom (i.e., —O-lower alkyl). Examples include, but are not limited to, methoxy, ethoxy, propoxy, isopropoxy, isobutoxy, and tertiary butoxy ($^t$OBu, or t-butoxy).

As used herein and unless otherwise indicated, the term "alcohol" means any compound substituted with an —OH group.

Unless otherwise indicated, the compounds of the invention, including intermediates useful for the preparation of the compounds of the invention, which contain reactive functional groups (such as, without limitation, carboxy, hydroxy, and amino moieties) also include protected derivatives thereof. "Protected derivatives" are those compounds in which a reactive site or sites are blocked with one or more protecting groups (also known as blocking groups). Suitable protecting groups for carboxy moieties include benzyl, t-butyl, and the like. Suitable protecting groups for amino and amido groups include acetyl, t-butyloxycarbonyl, benzyloxycarbonyl, and the like. Suitable protecting groups for hydroxy include benzyl and the like. Other suitable protecting groups are well known to those of ordinary skill in the art. The choice and use of protecting groups and the reaction conditions to install and remove protecting groups are described in T. W. Green, "Protective Groups in Organic Synthesis", Third Ed., Wiley, New York, 1999, which is incorporated herein by reference in its entirety.

As used herein and unless otherwise indicated, the term "substituted" as used to describe a compound or chemical moiety means that at least one hydrogen atom of that compound or chemical moiety is replaced with a second chemical moiety. The second chemical moiety may be any desired substituent that does not adversely affect the desired activity of the compound. Examples of substituents are those found in the exemplary compounds and embodiments disclosed herein, as well as halogen; $C_{1-8}$ alkyl; $C_{2-8}$ alkenyl; $C_{2-8}$ alkynyl; hydroxyl; $C_{1-6}$ alkoxyl; amino; nitro; thiol; thioether; imine; cyano; amido; phosphonato; phosphine; carboxyl; thiocarbonyl; sulfonyl; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); o-lower alkyl; o-aryl, aryl; aryl-lower alkyl; $CO_2CH_3$; $CONH_2$; $OCH_2CONH_2$; $NH_2$; $SO_2NH_2$; $OCHF_2$; $CF_3$; $OCF_3$; —NH(($C_1-C_8$)alkyl); —N(($C_1-C_8$)alkyl)$_2$; —NH(($C_6$)aryl); —N(($C_6$)aryl)$_2$; —CHO; —CO(($C_1-C_8$)alkyl); —CO(($C_6$)aryl); —CO$_2$(($C_1-C_8$)alkyl); and —CO$_2$(($C_6$)aryl); and such moieties may also be optionally substituted by a fused-ring structure or bridge, for example —OCH$_2$—. These substituents may optionally be further substituted with a substituent selected from such groups.

As used herein and unless otherwise indicated, a composition that is "substantially free" of a compound means that the composition contains less than about 20% by weight, more preferably less than about 10% by weight, even more preferably less than about 5% by weight, and most preferably less than about 3% by weight of the compound.

As used herein and unless otherwise indicated, the term "stereochemically pure" means a composition that comprises one stereoisomer of a compound and is substantially free of other stereoisomers of that compound.

As used herein and unless otherwise indicated, the term "enantiomerically pure" means a stereomerically pure composition of a compound having one chiral center.

As used herein and unless otherwise indicated, the term "racemic" or "racemate" means about 50% of one enantiomer and about 50% of the corresponding enantiomer relative to all chiral centers in the molecule. The invention encompasses all enantiomerically pure, enantiomerically enriched, diastereomerically pure, diastereomerically enriched, and racemic mixtures of the compounds of the invention.

As used herein and unless otherwise indicated, the term "process(es) of the invention" refers to the methods disclosed herein which are useful for preparing a compound of the invention. Modifications to the methods disclosed herein (e.g., starting materials, reagents, protecting groups, solvents, temperatures, reaction times, purification) are also encompassed by the present invention.

As used herein and unless otherwise indicated, the term "adding" or the like means contacting one reactant, reagent, solvent, catalyst, or the like with another reactant, reagent, solvent, catalyst, or the like. Reactants, reagents, solvents, catalysts, or the like can be added individually, simultaneously, or separately and can be added in any order. They can be added in the presence or absence of heat and can optionally be added under an inert atmosphere.

As used herein and unless otherwise indicated, the term "coupling" or the like means covalently linking two or more reactants via chemical reaction(s). The linking can be facilitated by acid(s), base(s), activating agent(s), catalyst(s), and so on. The linking can occur in the presence or absence of heat, light, sound (sonication), microwave radiation, and so on and can optionally occur under an inert atmosphere.

As used herein and unless otherwise indicated, a reaction that is "substantially complete" or is driven to "substantial completion" means that the reaction contains more than about 80% by percent yield, more preferably more than about 90% by percent yield, even more preferably more than about 95% by percent yield, and most preferably more than about 97% by percent yield of the desired product.

As used herein and unless otherwise indicated, the term "pharmaceutically acceptable salt" refers to a salt prepared from a pharmaceutically acceptable non-toxic inorganic or organic acid. Suitable non-toxic acids include, but are not limited to, acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, and p-toluenesulfonic acids. For example, specific pharmaceutically acceptable salts are hydrochloride, maleic acid, and tartaric acid salts.

As used herein and unless otherwise indicated, the term "hydrate" means a compound of the present invention or a salt thereof, that further includes a stoichiometric or non-stoichiometric amount of water bound by non-covalent intermolecular forces.

As used herein and unless otherwise indicated, the term "solvate" means a solvate formed from the association of one or more solvent molecules to a compound of the present invention. The term "solvate" includes hydrates (e.g., monohydrate, dihydrate, trihydrate, tetrahydrate, and the like).

As used herein and unless otherwise indicated, the term "polymorph" means solid crystalline forms of a compound of the present invention or complex thereof. Different polymorphs of the same compound may exhibit different physical, chemical and/or spectroscopic properties.

As used herein and unless otherwise indicated, the phrase "diseases or conditions related to an abnormally high level or activity of TNFα" means diseases or conditions that would not arise, endure, or cause symptoms if the level or activity of TNFα were lower, or diseases or conditions that can be prevented or treated by a lowering of TNFα level or activity.

As used herein and unless otherwise indicated, the term "treat", "treatment", "treating", or the like refers to the reduction or amelioration of the progression, severity and/or duration of a disease or condition, or the amelioration of one or more symptoms (preferably, one or more discernible symptoms) of a disease or condition resulting from the administration of one or more therapies (e.g., one or more therapeutic agents such as a compound of the invention).

As used herein and unless otherwise indicated, the term "prevent", "prevention", "preventing" or the like refers to the reduction in the risk of acquiring or developing a given disease or condition, or the reduction or inhibition of the recurrence, onset, or development of one or more symptoms of a given disease or condition.

Acronyms or symbols for groups or reagents have the following definition: ProtG=protecting group; Cbz=benzyloxycarbonyl; Boc=t-butyloxycarbonyl; Fmoc=9-fluorenylmethoxycarbonyl; p-TsOH=para-toluenesulfonic acid; TFA=trifluoroacetic acid; TMSCl=trimethylsilyl chloride; DMAP=N,N-dimethylaminopyridine; DBU=1,8-diazabicyclo[5.4.0]undec-7-ene; CDI=1,1'-carbonyldiimidazole; NBS=N-bromosuccinimide; VAZO®=1,1'-azobis-(cyclohexanecarbonitrile); DMF=N,N-dimethylformamide; THF=tetrahydrofuran; DCM=dichloromethane; MTBE=methyl tert-butyl ether.

If there is a discrepancy between a depicted structure and a name given that structure, the depicted structure is to be accorded more weight. Furthermore, if the stereochemistry of a structure or a portion thereof is not indicated, e.g., with bold or dashed lines, the structure or portion thereof is to be interpreted as encompassing all stereoisomers of it.

The invention can be understood more fully by reference to the following detailed description and illustrative examples, which are intended to exemplify non-limiting embodiments of the invention.

4.2 Processes of the Invention

The present invention provides cost-effective and efficient processes for the commercial production of substituted 2-(2, 6-dioxopiperidin-3-yl)-1-oxoisoindolines. In one embodiment, the invention provides a process for preparing a substituted 2-(2,6-dioxopiperidin-3-yl)-1-oxoisoindoline comprising the steps of: (1) protecting the α-amino group of a glutamine; (2) esterifying the N-protected glutamine; (3) deprotecting the α-amino group of the esterified glutamine; (4) coupling the N-deprotected glutamine ester with an optionally substituted 2-haloalklylbenzoate; (5) cyclizing the coupled product; and (6) optionally transforming one or more benzo substituents on the cyclized product into other substituent(s) in one or more steps. In one embodiment, the N-deprotected glutamine ester is a free amine. In another embodiment, the N-deprotected glutamine ester is an acid addition salt. In a particular embodiment, the N-deprotected glutamine ester is a hydrochloride salt.

In another embodiment, the invention provides a process for preparing a substituted 2-(2,6-dioxopiperidin-3-yl)-1-oxoisoindoline comprising the steps of: (1) esterifying glutamine; (2) coupling the esterified glutamine with an optionally substituted 2-haloalklylbenzoate; (3) cyclizing the coupled product; and (4) optionally transforming one or more benzo substituents on the cyclized product into other substituent(s) in one or more steps. In one embodiment, the esterified glutamine is a free amine. In another embodiment, the esterified glutamine is an acid addition salt. In a particular embodiment, the esterified glutamine is a hydrochloride salt.

In yet another embodiment, the invention provides a process for preparing a substituted 2-(2,6-dioxopiperidin-3-yl)-1-oxoisoindoline comprising the steps of: (1) protecting the α-amino group of a glutamine; (2) esterifying the N-protected glutamine; (3) deprotecting the α-amino group of the esterified glutamine; (4) coupling the N-deprotected glutamine ester with an optionally substituted 2-haloalklylbenzoate; (5) transforming one or more benzo substituents on the coupled product into other substituent(s) in one or more steps; and (6) cyclizing the transformed product. In one embodiment, the N-deprotected glutamine ester is a free amine. In another embodiment, the N-deprotected glutamine ester is an acid addition salt. In a particular embodiment, the N-deprotected glutamine ester is a hydrochloride salt.

In still another embodiment, the invention provides a process for preparing a substituted 2-(2,6-dioxopiperidin-3-yl)-1-oxoisoindoline comprising the steps of: (1) esterifying glutamine; (2) coupling the esterified glutamine with an optionally substituted 2-haloalklylbenzoate; (3) transforming one or more benzo substituents on the coupled product into other substituent(s) in one or more steps; and (4) cyclizing the transformed product. In one embodiment, the esterified glutamine is a free amine. In another embodiment, the esterified glutamine is an acid addition salt. In a particular embodiment, the esterified glutamine is a hydrochloride salt.

In one embodiment, the invention relates to a process for preparing a compound of Formula I:

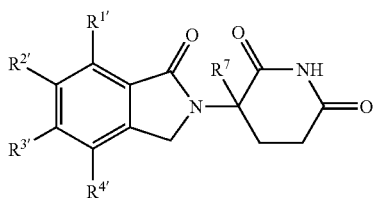

or a pharmaceutically acceptable salt, hydrate, solvate, or polymorph thereof, wherein:

each of $R^{1'}$, $R^{2'}$, $R^{3'}$, and $R^{4'}$ is at each occurrence independently hydrogen, halo, alkyl, alkoxy, —$CF_3$, —CN, —$NO_2$, —$NHProtG^2$, or —$NR^5R^6$;

each of $R^5$ and $R^6$ is at each occurrence independently hydrogen or alkyl;

$R^7$ is hydrogen, halo, alkyl, or benzyl; and $ProtG^2$ is a suitable N-protecting group, which comprises the alternative sequences of steps of:

(1)(a) coupling a glutamine ester or a salt thereof with an optionally substituted 2-haloalklylbenzoate;

(b) cyclizing the coupled product; and (c) optionally transforming one or more benzo substituents of the cyclized product into other substituent(s) in one or more steps, or:

(2)(a) coupling a glutamine ester or a salt thereof with an optionally substituted 2-haloalklylbenzoate;

(b) transforming one or more benzo substituents of the coupled product into other substituent(s) in one or more steps; and (c) cyclizing the transformed product.

For the above embodiments, the α-amino group of a glutamine can be protected as, for example, an amide (e.g., a trifluoroacetamide) or as a carbamate (e.g., a Cbz, Boc, or Fmoc carbamate). The N-protecting group can be removed in various ways, including, but not limited to, by catalytic hydrogenolysis (e.g., for a Cbz carbamate), under acidic condition (e.g., for a Boc carbamate), or under basic condition (e.g., for a Fmoc carbamate or a trifluoroacetamide). The carboxyl group of an N-protected or N-unprotected glutamine can be esterified as, for example, an alkyl or a benzyl ester. Various methods of esterification are well known in the art. For example, esterification can occur in the corresponding alcohol under acidic condition. The corresponding alcohol can also be used in the presence of an activating agent such as, e.g., a carbodiimide to esterify. Esterification can also be effected using a corresponding alkyl or benzyl halide under basic condition.

A glutamine ester or a salt thereof can be coupled to an optionally substituted 2-haloalklylbenzoate under basic conditions. The optionally substituted 2-haloalklylbenzoate can be generated by halogenating the corresponding an optionally substituted 2-alklylbenzoate, e.g., using an appropriate halogenating agent under free-radical condition. Cyclization to form a 2,6-piperidinedione moiety can occur under acidic or basic conditions with an ester group as the accepting group. Cyclization can also be effected in the presence of an activating agent (e.g., thionyl chloride, oxalyl chloride, CDI, and the like) with a carboxyl group as the accepting group. Among the various possible kinds of transformation of benzo substituents, a benzo —$NO_2$ group can be reduced to an —$NH_2$ group and a protected benzo —$NHProtG^2$ group can be deblocked to yield an —$NH_2$ group.

In yet other embodiments, the present invention provides processes for preparing substituted 2-(2,6-dioxopiperidin-3-yl)-1-oxoisoindolines as set forth in Scheme 1. In these embodiments:

(a) each of $R^1$, $R^2$, $R^3$, $R^4$, $R^{1'}$, $R^{2'}$, $R^{3'}$, and $R^{4'}$ is at each occurrence independently hydrogen, halo, alkyl, alkoxy, —$CF_3$, —CN, —$NO_2$, —$NHProtG^2$, or —$NR^5R^6$;

(b) each of $R^5$ and $R^6$ is at each occurrence independently hydrogen or alkyl;

(c) $R^7$ is hydrogen, halo, alkyl, or benzyl;

(d) $R^8$ is hydrogen, alkyl, or benzyl;

(e) $R^9$ is alkyl;

(f) X is halo; and (g) each of $ProtG^1$ and $ProtG^2$ is at each occurrence independently a suitable N-protecting group.

$R^{1'}$, $R^{2'}$, $R^{3'}$, and $R^{4'}$ denote that one or more of the $R^1$, $R^2$, $R^3$, and/or $R^4$ substituents are optionally transformed to the corresponding $R^{1'}$, $R^{2'}$, $R^{3'}$, and/or $R^{4'}$ substituents, respectively, in one or more steps.

Scheme 1

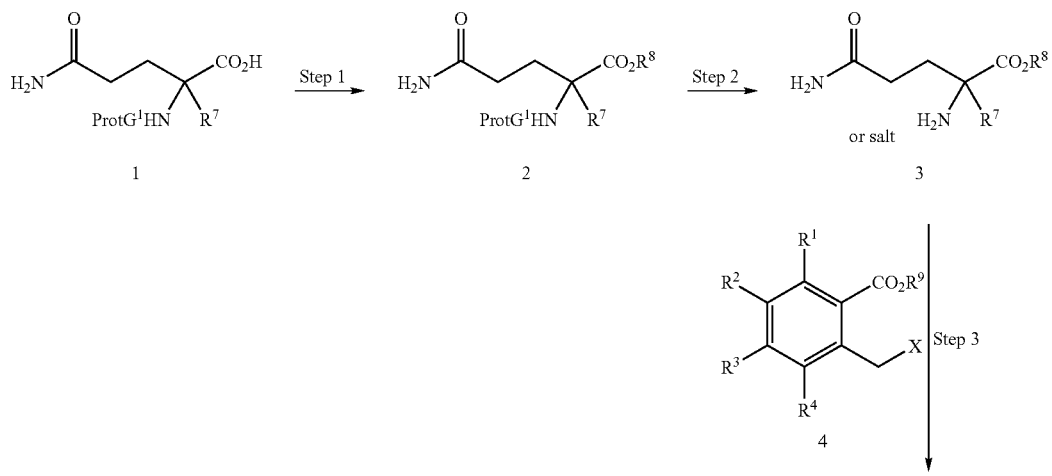

-continued

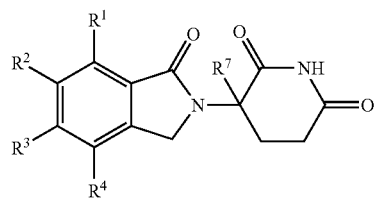

6

Step 4 ←

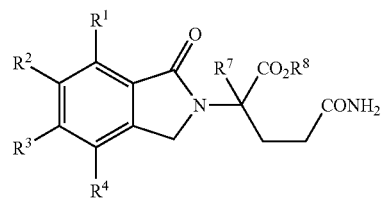

5

Step 5 ↓

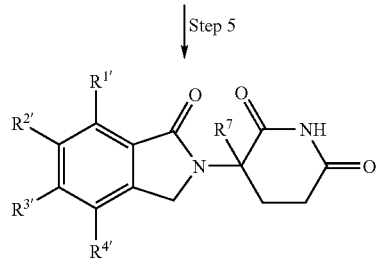

I

Step 7 ←

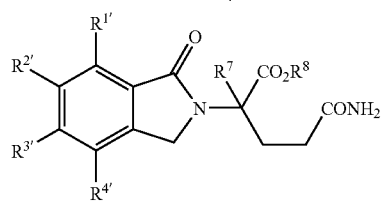

7

Step 6 ↓

In one embodiment of Scheme 1:

(a) each of $R^1$, $R^2$, $R^3$, $R^4$, $R^{1'}$, $R^{2'}$, $R^{3'}$, and $R^{4'}$ is at each occurrence independently hydrogen, lower molecular weight halo, lower alkyl, lower alkoxy, —$NO_2$, —$NHProtG^2$, or —$NR^5R^6$;

(b) each of $R^5$ and $R^6$ is at each occurrence independently hydrogen or lower alkyl;

(c) $R^7$ is hydrogen or lower alkyl;

(d) $R^8$ is hydrogen, lower alkyl, or benzyl;

(e) $R^9$ is lower alkyl;

(f) X is higher molecular weight halo; and (g) each of $ProtG^1$ and $ProtG^2$ is at each occurrence independently a suitable acyl N-protecting group.

In another embodiment of Scheme 1:

(a) each of $R^1$, $R^2$, $R^3$, and $R^4$ is at each occurrence independently hydrogen, —$NO_2$, or —$NHProtG^2$;

(b) each of $R^{1'}$, $R^{2'}$, $R^{3'}$, and $R^{4'}$ is at each occurrence independently hydrogen, —$NHProtG^2$, or —$NH_2$;

(c) $R^7$ is hydrogen or methyl;

(d) $R^8$ is hydrogen or methyl;

(e) $R^9$ is methyl;

(f) X is bromo;

(g) $ProtG^1$ is Cbz or Boc; and (h) $ProtG^2$ is Cbz, Boc, formyl, acetyl, trifluoroacetyl, or pivaloyl.

In one embodiment, the invention relates to a process for preparing a compound of Formula I:

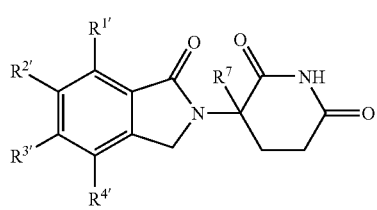

I or a pharmaceutically acceptable salt, hydrate, solvate, or polymorph thereof, wherein:

each of $R^{1'}$, $R^{2'}$, $R^{3'}$, and $R^{4'}$ is at each occurrence independently hydrogen, halo, alkyl, alkoxy, —$CF_3$, —CN, —$NO_2$, —$NHProtG^2$, or —$NR^5R^6$;

each of $R^5$ and $R^6$ is at each occurrence independently hydrogen or alkyl;

$R^7$ is hydrogen, halo, alkyl, or benzyl; and $ProtG^2$ is a suitable N-protecting group, which comprises the alternative sequences of steps of:

(1)(a) cyclizing a compound of Formula 5:

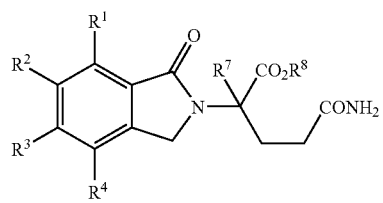

5 and (b) optionally transforming one or more of the $R^1$, $R^2$, $R^3$, and/or $R^4$ substituents of the cyclized product of Formula 6:

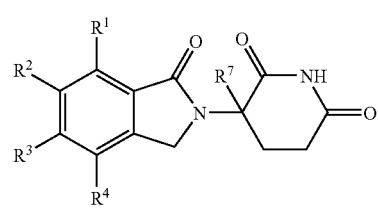

6 into one or more of the corresponding $R^{1'}$, $R^{2'}$, $R^{3'}$, and/or $R^{4'}$ substituents, respectively, of the compound of Formula I in one or more steps, or:

(2)(a) transforming one or more of the $R^1$, $R^2$, $R^3$, and/or $R^4$ substituents of a compound of Formula 5:

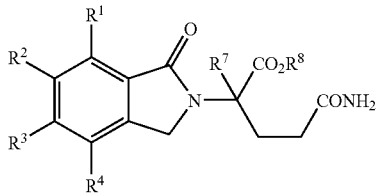

into one or more of the corresponding $R^{1'}$, $R^{2'}$, $R^{3'}$, and/or $R^{4'}$ substituents, respectively, of a compound of Formula 7:

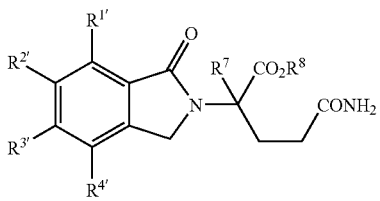

in one or more steps, and (b) cyclizing the transformed product of Formula 7, wherein, for both sequences of steps unless noted otherwise:
each of $R^1$, $R^2$, $R^3$, $R^4$, $R^{1'}$, $R^{2'}$, $R^{3'}$, and $R^{4'}$ is at each occurrence independently hydrogen, halo, alkyl, alkoxy, —$CF_3$, —CN, —$NO_2$, —$NHProtG^2$, or —$NR^5R^6$;
each of $R^5$ and $R^6$ is at each occurrence independently hydrogen or alkyl;
$R^7$ is hydrogen, halo, alkyl, or benzyl;
$R^8$ is alkyl or benzyl for sequence (1) and is hydrogen, alkyl, or benzyl for sequence (2); and
$ProtG^2$ is a suitable N-protecting group.

In one embodiment of Scheme 1, an N-protected glutamine 1 is esterified in step 1. The N-protected glutamine may be commercially available or prepared by protecting the α-amino group of a glutamine as is known in the art (See, e.g., T. W. Green, "Protective Groups in Organic Synthesis", Third Ed., Wiley, New York, 1999). In one embodiment, $ProtG^1$ is a suitable N-protecting group and $R^8$ is lower alkyl or benzyl. In a particular embodiment, $ProtG^1$ is Cbz and $R^8$ is methyl. The selection of $R^8$ and of the conditions for esterification depends, inter alia, upon the nature of the N-blocking group. In one embodiment, $ProtG^1$ is Fmoc, $R^8$ is t-butyl, and esterification is conducted employing 2-methyl-prop-1-ene and a catalytic amount of acid. In another embodiment, $ProtG^1$ is Boc, $R^8$ is methyl, and esterification is effected using MeI and DBU.

In yet another embodiment, $ProtG^1$ is Cbz, $R^8$ is lower alkyl, and esterification is conducted in the corresponding lower alcohol under acidic condition. In a further embodiment, esterification is conducted in the lower alcohol in the presence of catalytic amount of activating agent(s). In a particular embodiment, the activating agent is TMSCl. In another particular embodiment, the activating agent is acetyl chloride. In yet another particular embodiment, the activating agents are TMSCl and acetyl chloride. Esterification in the lower alcohol is performed at an elevated temperature in one embodiment. In a particular embodiment, esterification in the lower alcohol is performed at a temperature at which the lower alcohol refluxes. Esterification in the lower alcohol is generally conducted until the reaction is substantially complete. In an embodiment, esterification in the lower alcohol is conducted for at least about 4 hours. In a particular embodiment, $ProtG^1$ is Cbz, $R^8$ is methyl, and esterification is conducted in methanol.

In step 2 of Scheme 1, the N-protecting group of ester 2 is cleaved. In one embodiment, N-deprotected ester 3 is a free amine. In another embodiment, N-deprotected ester 3 is an acid addition salt. In a particular embodiment, N-deprotected ester 3 is a hydrochloride salt. The selection of $ProtG^1$ and of the conditions for the cleavage of the N-blocking group depends, inter alia, upon the nature of the ester group $R^8$. In one embodiment, $R^8$ is lower alkyl or benzyl, $ProtG^1$ is Boc, and the N-Boc group is cleaved under acidic condition. In a particular embodiment, the N-Boc group is cleaved using TFA. In another particular embodiment, the N-Boc group is cleaved using HCl. In another embodiment, $R^8$ is t-butyl, $ProtG^1$ is Fmoc, and the N-Fmoc group is cleaved under basic condition. In an embodiment, the N-Fmoc group is cleaved using piperidine.

In a further embodiment, $R^8$ is lower alkyl, $ProtG^1$ is Cbz, and the N-Cbz group is cleaved by catalytic hydrogenolysis under hydrogen. In one embodiment, the N-Cbz group is cleaved using a metal catalyst. In a further embodiment, the metal catalyst is a Pd catalyst. In a particular embodiment, the catalyst is 5% Pd/C. In another particular embodiment, the catalyst is 10% Pd/C. The hydrogenolysis is generally conducted under a hydrogen pressure that drives the reaction to substantial completion. In an embodiment, the hydrogenolysis is conducted under a hydrogen pressure of about 40 to 50 psi. The hydrogenolysis is done in a protic solvent in one embodiment. In a further embodiment, the protic solvent is a lower alcohol. In a particular embodiment, the solvent is methanol. In another particular embodiment, the solvent is ethanol. The hydrogenolysis is done in an aprotic solvent in another embodiment. In a particular embodiment, the aprotic solvent is ethyl acetate. The hydrogenolysis is done in a mixture of protic solvent and aprotic solvent in yet another embodiment. In an embodiment, the mixture of protic and aprotic solvents comprises a lower alcohol and ethyl acetate. In a particular embodiment, the mixture of protic and aprotic solvents comprises methanol and ethyl acetate. In another particular embodiment, the mixture of protic and aprotic solvents comprises ethanol and ethyl acetate. The hydrogenolysis is performed in the absence of added acid in one embodiment. In another embodiment, the hydrogenolysis is performed in the presence of added acid. In a particular embodiment, the added acid is HCl. The hydrogenolysis is generally conducted until the reaction is substantially complete. In one embodiment, the hydrogenolysis is conducted for at least about 3 hours.

In another embodiment of Scheme 1, ester 3 may be formed directly from a glutamine whose amino and carboxyl groups are unprotected. Ester 3 is a free amine in one embodiment. In another embodiment, ester 3 is an acid addition salt. In a particular embodiment, ester 3 is a hydrochloride salt. In one embodiment, $R^8$ is lower alkyl and esterification occurs in the corresponding lower alcohol under acidic condition. In a further embodiment, esterification is conducted in the lower alcohol in the presence of catalytic amount of activating agent(s). In a particular embodiment, the activating agent is TMSCl. In another particular embodiment, the activating agent is acetyl chloride. In yet another particular embodiment, the activating agents are TMSCl and acetyl chloride. Esterification in the lower alcohol is performed at an elevated temperature in one embodiment. In a particular embodiment, esterification in the lower alcohol is performed at a temperature at which the lower alcohol refluxes. Esterification in the lower alcohol is generally conducted until the reaction is substantially complete. In an embodiment, esterification in the lower alcohol is conducted for at least about 4 hours. In a particular embodiment, $R^8$ is methyl, and esterification is conducted in methanol. Furthermore, an acid addition salt of ester 3 may be commercially available, such as glutamine methyl ester hydrochloride.

In step 3 of Scheme 1, a benzyl halide 4 is coupled to a free amine 3 in one embodiment or to an acid addition salt 3 in another embodiment. The coupling occurs in the presence of a base in one embodiment. In one embodiment, the base is an alkyl amine. In a particular embodiment, the base is $NEt_3$. In a further embodiment, the base is $iPrEt_2N$. In another embodiment, the base is a carbonate or bicarbonate. In a particular embodiment, the base is $NaHCO_3$. In yet another embodiment, the base is a pyridine. In a particular embodiment, the base is 4-DMAP. The coupling is conducted in a polar solvent in one embodiment. In a further embodiment, the polar solvent is aprotic. In a particular embodiment, the solvent is DMF. In another particular embodiment, the solvent is acetonitrile. In yet another particular embodiment, the solvent is THF. The coupling is performed at ambient temperature in one embodiment. In another embodiment, the coupling is performed at elevated temperature. In a particular embodiment, the coupling is performed at a temperature at which the solvent refluxes. The coupling is generally conducted until the reaction is substantially complete. In one embodiment, the coupling is conducted for at least about 1 hour.

Benzyl halide 4 can be generated by halogenating the corresponding optionally substituted 2-alklylbenzoate. X is halo in one embodiment. In another embodiment, X is higher molecular weight halo. In a particular embodiment, X is bromo and benzyl bromide 4 is prepared by brominating the corresponding optionally substituted 2-alklylbenzoate with a brominating agent in the presence of a radical initiator. In a particular embodiment, the brominating agent is NBS. The radical initiator is light in a particular embodiment and VAZO® (i.e., 1,1'-azobis-(cyclohexanecarbonitrile)) in another particular embodiment. $R^9$ is lower alkyl in an embodiment. In a particular embodiment, $R^9$ is methyl.

From common intermediate 5 in Scheme 1, cyclization to form the 2,6-piperidinedione ring and optional transformation of one or more benzo substituents $R^1$, $R^2$, $R^3$, and/or $R^4$ in one or more steps can occur in different order. In one embodiment, cyclization transpires in step 4 prior to optional transformation of one or more benzo substituents in step 5 (which may comprise one or more steps). Both compounds 6 and I are substituted 2-(2,6-dioxopiperidin-3-yl)-1-oxoisoindolines.

In one embodiment, cyclization in step 4 of Scheme 1 occurs with an ester group as the accepting group. In an embodiment, $R^8$ is lower alkyl. In a particular embodiment, $R^8$ is methyl. Cyclization is effected in the presence of an acid in one embodiment. In a further embodiment, a catalytic amount of acid is used. In a particular embodiment, the acid is p-TsOH. Cyclization under acidic condition is conducted in an aprotic solvent in one embodiment. In a further embodiment, the aprotic solvent is apolar. In a particular embodiment, the solvent is toluene. Cyclization occurs at ambient temperature in an embodiment. In another embodiment, cyclization occurs at elevated temperature. In a particular embodiment, cyclization occurs at a temperature at which the solvent refluxes.

Cyclization with an ester group as the accepting group occurs in the presence of a base in another embodiment. In one embodiment, the base is an alkoxide. In a further embodiment, the base is a sterically bulky alkoxide. In a particular embodiment, the base is $KO^tBu$. In another embodiment, the base is a carbonate. In a particular embodiment, the base is $K_2CO_3$. Cyclization under basic condition is conducted in an aprotic solvent in one embodiment. In a further embodiment, the aprotic solvent is polar. In a particular embodiment, the solvent is THF. In another particular embodiment, the solvent is acetonitrile. Cyclization is generally conducted at a temperature that drives the reaction to substantial completion. In an embodiment, cyclization is conducted at ambient temperature. In another embodiment, cyclization is conducted at a temperature below ambient temperature. In a particular embodiment, cyclization is conducted at between about 0 and 5° C. Cyclization is conducted at elevated temperature in yet another embodiment. In a particular embodiment, cyclization is conducted at a temperature at which the solvent refluxes. Cyclization is generally performed until the reaction is substantially complete. In an embodiment, cyclization is performed for at least about 0.5 hour.

In another embodiment, cyclization occurs with a carboxyl group as the accepting group (i.e., $R^8$ is hydrogen). In one embodiment, cyclization is effected with an activating agent that activates the carboxyl group. In a particular embodiment, the activating agent is thionyl chloride. In another particular embodiment, the activating agent is CDI. Cyclization is effected in the presence of a second activating agent in another embodiment. In a particular embodiment, the second activating agent is 4-DMAP. Cyclization occurs in the presence of a base in one embodiment. In an embodiment, the base is an alkyl amine. In a particular embodiment, the base is $NEt_3$. In a further embodiment, the base is $iPrEt_2N$. In another embodiment, the base belongs to the pyridine family of amines. In a particular embodiment, the base is pyridine. Cyclization occurs in the presence of a mixture of bases in another embodiment. In an embodiment, the mixture of bases comprises an alkyl amine and an amine belonging to the pyridine family of amines. In a particular embodiment, the mixture of bases is $NEt_3$ and pyridine. Cyclization is conducted in an aprotic solvent in one embodiment. In a further embodiment, the aprotic solvent is polar. In a particular embodiment, the solvent is DCM. In another particular embodiment, the solvent is THF. Cyclization is generally conducted at a temperature that drives the reaction to substantial completion. In an embodiment, cyclization is conducted at a range of temperature below and including ambient temperature. In a particular embodiment, cyclization is conducted from about −30° C. to ambient temperature. Cyclization is conducted at elevated temperature in another embodiment. In a particular embodiment, cyclization is conducted at a temperature at which the solvent refluxes. Cyclization is generally performed until the reaction is substantially complete. In an embodiment, cyclization is performed for at least about 3 hours.

If cyclization with a carboxyl group as the accepting group is desired, the carboxyl group can be generated from an ester group in various ways after coupling of amine or acid addition salt 3 to benzyl halide 4, depending upon, inter alia, the nature of the ester group and the nature of the other functional groups in intermediate 5. In one embodiment, $R^8$ is benzyl, and the benzyl ester is converted to a carboxyl group by hydrogenolysis with a catalyst. In an embodiment, the catalyst is a metal catalyst. In a further embodiment, the catalyst is a Pd catalyst and, in a particular embodiment, a Pd/C catalyst. In another embodiment, $R^8$ is t-butyl, and the t-butyl ester is converted to a carboxyl group in the presence of an acid. The acid is TFA in a particular embodiment and HCl in another particular embodiment. In yet another embodiment, $R^8$ is lower alkyl. $R^8$ is methyl in a particular embodiment. In an embodiment, the lower alkyl ester is converted to a carboxyl group in the presence of acid and water. In another embodiment, the lower alkyl ester is converted to a carboxyl group (after appropriate acidifying workup) in the presence of a base. In an embodiment, the base is a hydroxide. The base is LiOH in a particular embodiment, NaOH in another particular embodiment, and KOH in yet another particular embodiment.

If a racemic substituted 2-(2,6-dioxopiperidin-3-yl)-1-oxoisoindoline is desired, conducting the cyclization with an ester group as the accepting group under basic condition offers an advantage. Base may racemize any chiral stereocenter to which $R^7$ is attached, where $R^7$ is hydrogen. Conversely, if an enantiomerically pure substituted 2-(2,6-dioxopiperidin-3-yl)-1-oxoisoindoline is desired, conducting the cyclization with an ester group as the accepting group under acidic condition or with a carboxyl group as the accepting group in the presence of activating agent(s) may be beneficial. In these two latter scenarios, the reaction conditions may result in retention of the stereochemistry of any chiral stereocenter to which $R^7$ is attached.

After cyclization to form the glutarimide ring, one or more benzo $R^1$, $R^2$, $R^3$, and/or $R^4$ substituents may optionally be transformed to the corresponding $R^{1'}$, $R^{2'}$, $R^{3'}$, and/or $R^{4'}$ substituents, respectively, in one or more steps (summarized as step 5 of Scheme 1). In one embodiment, one of $R^1$, $R^2$, $R^3$, or $R^4$ is —$NO_2$ and it is reduced to —$NH_2$ for the corresponding $R^{1'}$, $R^{2'}$, $R^{3'}$, or $R^{4'}$, respectively. In a particular embodiment, $R^4$ is —$NO_2$ and it is reduced to —$NH_2$ for $R^{4'}$. The reduction of —$NO_2$ to —$NH_2$ is effected under hydrogen with a metal catalyst in one embodiment. In a further embodiment, the catalyst is a Pd catalyst. In a particular embodiment, the catalyst is 10% Pd/C. In another particular embodiment, the catalyst is 5% Pd/C. The reduction is conducted in a protic solvent in one embodiment. In a further embodiment, the protic solvent is an alcohol, in one embodiment a lower alcohol. The solvent is ethanol in a particular embodiment and methanol in another particular embodiment. In another embodiment the solvent is propanol, isopropanol, butanol, isobutanol or t-butanol. In another embodiment, the reduction is conducted in an apolar, aprotic solvent. The solvent is 1,4-dioxane in a particular embodiment. In yet another embodiment, the reduction is conducted in a polar, aprotic solvent. The solvent is acetone in a particular embodiment. In another embodiment, the solvent is DMSO, DMF or THF. The reduction is generally carried out at a hydrogen pressure that drives the reaction to substantial completion. In a particular embodiment, the reduction is carried out at a hydrogen pressure between about 40 and 50 psi. In an embodiment, the reduction is run at ambient temperature. The reduction is generally performed until the reaction is substantially complete. In an embodiment, the reduction is performed for at least about 2 hours.

In another embodiment, one of $R^1$, $R^2$, $R^3$, or $R^4$ is —$NHProtG^2$ and it is deprotected to give —$NH_2$ for the corresponding $R^{1'}$, $R^{2'}$, $R^{3'}$, or $R^{4'}$, respectively. In a particular embodiment, $R^4$ is —$NHProtG^2$ and it is deprotected to give —$NH_2$ for $R^{4'}$. In one embodiment, the protecting group $ProtG^2$ for a benzo —$NHProtG^2$ substituent is an acyl group which is selectively removable under mild condition. $ProtG^2$ is formyl in a particular embodiment and acetyl in another particular embodiment. In a further embodiment, $ProtG^2$ is a lower alkanoyl group which is branched in the position α to the carbonyl group. $ProtG^2$ is pivaloyl in a particular embodiment and trifluoroacetyl in another particular embodiment. In a particular embodiment, a benzo —$NHC(O)CF_3$ group is deblocked under basic condition. In another embodiment, —$NHProtG^2$ is a carbamate. $ProtG^2$ is Boc in a particular embodiment and Cbz in another particular embodiment. In particular embodiments, a benzo —NHBoc group is deprotected under acidic condition and a benzo —NHCbz group is deblocked by hydrogenolysis with a catalyst.

The choice of $ProtG^2$ depends, inter alia, upon the stability of the protecting group under reaction conditions where its cleavage is not desired and upon the stability of other functional groups under the conditions required to remove the protecting group. The various choices for $ProtG^2$ and the conditions to remove it are well known in the art, as, e.g., described in T. W. Green, "Protective Groups in Organic Synthesis", Third Ed., Wiley, New York, 1999. Substituted 2-(2,6-dioxopiperidin-3-yl)-1-oxoisoindolines with benzo —$NHProtG^2$ substituent(s) intact may also exhibit biological properties, and thus the removal of $ProtG^2$ may not be desired.

From common intermediate 5 in Scheme 1, one or more benzo $R^1$, $R^2$, $R^3$, and/or $R^4$ substituents can alternatively be transformed to the corresponding $R^{1'}$, $R^{2'}$, $R^{3'}$, and/or $R^{4'}$ substituents, respectively, in one or more steps (summarized as step 6) before cyclization of oxoisoindoline 7 in step 7 produces substituted 2-(2,6-dioxopiperidin-3-yl)-1-oxoisoindoline I. The above description of cyclization in step 4 and transformation of benzo substitutent(s) in step 5 and further embodiments described herein for steps 4 and 5 generally apply to transformation of benzo substituent(s) in step 6 and cyclization in step 7. Furthermore, if cyclization is done in step 7 with a carboxyl group as the accepting group, compound 7 having $R^8$ as hydrogen can be generated from the corresponding compound 7 having $R^8$ as alkyl or benzyl.

Whether cyclization is performed prior to conversion of benzo substituent(s) or conversion of benzo substituent(s) is performed prior to cyclization may depend upon various factors. For example, if transformation of a benzo substituent results in another substituent that is not compatible with desired conditions for cyclization, then conducting cyclization in step 4 prior to transformation of the benzo substituent in step 5 may be desired.

Scheme 2 illustrates particular embodiments of the synthesis of mono-benzo-substituted 2-(2,6-dioxopiperidin-3-yl)-1-oxoisoindolines. In these embodiments:

(a) each of $R^1$ and $R^2$ is at each occurrence independently halo, alkyl, alkoxy, —$CF_3$, —CN, —$NO_2$, —$NHProtG^2$, or —$NR^5R^6$, and can occupy any position on the benzo ring;

(b) each of $R^5$ and $R^6$ is at each occurrence independently hydrogen or alkyl;

(c) $R^7$ is hydrogen, halo, alkyl, or benzyl;

(d) $R^8$ is hydrogen, alkyl, or benzyl;

(e) $R^9$ is alkyl;

(f) X is halo; and (g) each of $ProtG^1$ and $ProtG^2$ is at each occurrence independently a suitable N-protecting group.

$R^2$ denotes that $R^1$ may optionally be transformed to $R^2$.

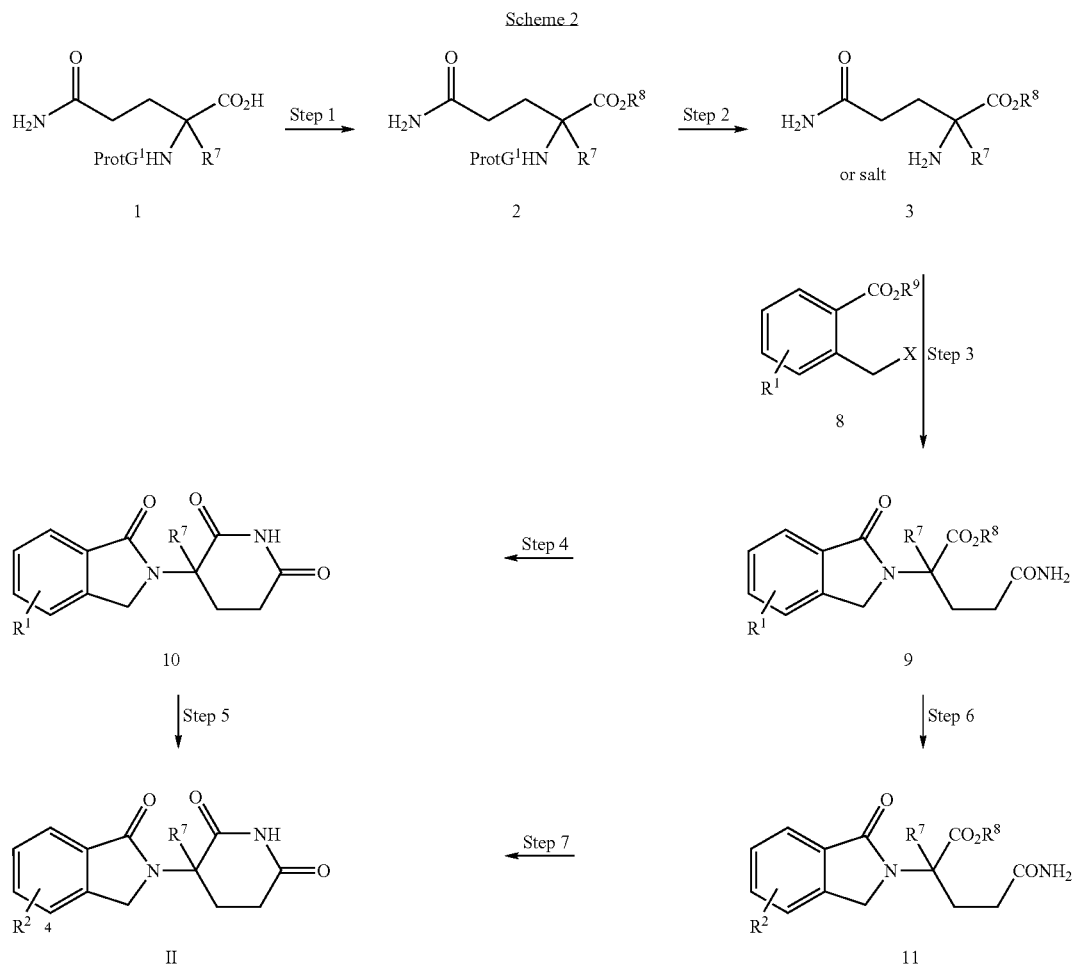

Scheme 2

In one embodiment of Scheme 2:

(a) each of $R^1$ and $R^2$ is at each occurrence independently lower molecular weight halo, lower alkyl, lower alkoxy, $-NO_2$, $-NHProtG^2$, or $-NR^5R^6$, and can occupy any position on the benzo ring;

(b) each of $R^5$ and $R^6$ is at each occurrence independently hydrogen or lower alkyl;

(c) $R^7$ is hydrogen or lower alkyl;

(d) $R^8$ is hydrogen, lower alkyl, or benzyl;

(e) $R^9$ is lower alkyl;

(f) X is higher molecular weight halo; and (g) each of $ProtG^1$ and $ProtG^2$ is at each occurrence independently a suitable acyl N-protecting group.

In another embodiment of Scheme 2:

(a) $R^1$ is $-NO_2$ or $-NHProtG^2$ and can occupy any position on the benzo ring;

(b) $R^2$ is $-NH_2$ and occupies the same position on the benzo ring as $R^1$;

(c) $R^7$ is hydrogen or methyl;

(d) $R^8$ is hydrogen or methyl;

(e) $R^9$ is methyl;

(f) X is bromo;

(g) $ProtG^1$ is Cbz or Boc; and (h) $ProtG^2$ is Cbz, Boc, formyl, acetyl, trifluoroacetyl, or pivaloyl.

In one embodiment, the invention relates to a process for preparing a compound of Formula II:

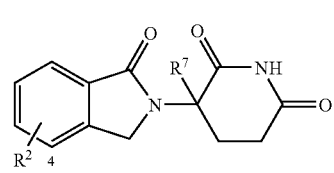

or a pharmaceutically acceptable salt, hydrate, solvate, or polymorph thereof, wherein:

$R^2$ is halo, alkyl, alkoxy, $-CF_3$, $-CN$, $-NO_2$, $-NHProtG^2$, or $-NR^5R^6$;

each of $R^5$ and $R^6$ is at each occurrence independently hydrogen or alkyl;

$R^7$ is hydrogen, halo, alkyl, or benzyl; and $ProtG^2$ is a suitable N-protecting group, which comprises the alternative sequences of steps of:

(1)(a) cyclizing a compound of Formula 9:

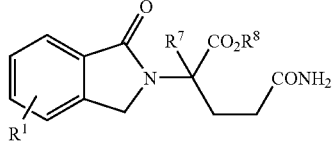

and (b) optionally transforming the $R^1$ substituent of the cyclized product of Formula 10:

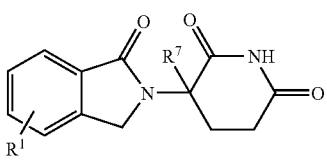

into the $R^2$ substituent of the compound of Formula II, or:

(2)(a) transforming the $R^1$ substituent of a compound of Formula 9:

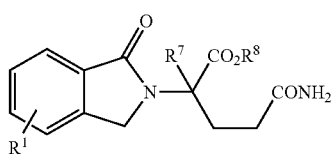

into the $R^2$ substituent of a compound of Formula 11:

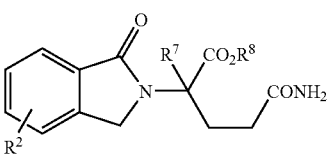

and (b) cyclizing the transformed product of Formula 11, wherein, for both sequences of steps unless noted otherwise:

each of $R^1$ and $R^2$ is at each occurrence independently halo, alkyl, alkoxy, —$CF_3$, —CN, —$NO_2$, —$NHProtG^2$, or —$NR^5R^6$;

each of $R^5$ and $R^6$ is at each occurrence independently hydrogen or alkyl;

$R^7$ is hydrogen, halo, alkyl, or benzyl;

$R^8$ is alkyl or benzyl for sequence (1) and is hydrogen, alkyl, or benzyl for sequence (2); and $ProtG^2$ is a suitable N-protecting group.

The description of Scheme 1 and further embodiments described herein for Scheme 1 generally apply to Scheme 2. Specifically, the description of steps 1, 2, 3, 4, 5, 6, and 7 in Scheme 1 and further embodiments described herein for Scheme 1 generally apply to the corresponding steps 1, 2, 3, 4, 5, 6, and 7, respectively, in Scheme 2.

Cyclization to form the 2,6-piperidinedione ring and optional transformation of benzo substituent $R^1$ to $R^2$ can occur in different order from common intermediate 9 in Scheme 2. In one embodiment, cyclization transpires in step 4 prior to transformation of the benzo substituent in step 5. Both compounds 10 and II are mono-benzo-substituted 2-(2, 6-dioxopiperidin-3-yl)-1-oxoisoindolines. In another embodiment, the benzo substituent is transformed in step 6 before cyclization in step 7 produces II.

Cyclization of the glutamine side chain in step 4 or step 7 of Scheme 2 can be effected in various ways. In one embodiment, cyclization occurs under acidic condition with an ester group (e.g., $R^8$ is lower alkyl) as the accepting group. In another embodiment, cyclization occurs under basic condition with an ester group (e.g., $R^8$ is lower alkyl) as the accepting group. Under acidic or basic condition, $R^8$ is methyl in a particular embodiment. In yet another embodiment, cyclization occurs in the presence of activating agent(s) with a carboxyl group (i.e., $R^8$ is hydrogen) as the accepting group.

The choice of cyclization conditions may depend, inter alia, upon the desired stereochemistry of the cyclized product. Cyclization with an ester group as the accepting group under basic conditions may result in racemization of any chiral stereocenter to which $R^7$ is attached, where $R^7$ is hydrogen. By contrast, cyclization with an ester group as the accepting group under acidic conditions or with a carboxyl group as the accepting group in the presence of activating agent(s) may lead to retention of the stereochemistry of any chiral stereocenter to which $R^7$ is attached.

There are numerous possible kinds of conversion of benzo substituent $R^1$ to $R^2$, if desired. In one embodiment, $R^1$ is —$NO_2$ and it is reduced to —$NH_2$. In a particular embodiment, $R^1$ is 4-$NO_2$ and it is reduced to 4-$NH_2$. Reduction of the benzo nitro group is facilitated by a metal catalyst in one embodiment. The catalyst is a Pd catalyst in a further embodiment and a Pd/C catalyst in a particular embodiment. In another embodiment, $R^1$ is —$NHProtG^2$ and the protecting group $ProtG^2$ is cleaved to give —$NH_2$. $R^1$ is 4-$NHProtG^2$ and $ProtG^2$ is removed to give 4-$NH_2$ in a particular embodiment. In yet another embodiment, $ProtG^2$ is Cbz and it is removed by hydrogenolysis with a metal catalyst. The catalyst is a Pd catalyst in a further embodiment and a Pd/C catalyst in a particular embodiment. If a benzo —$NO_2$ group is reduced to —$NH_2$ with a metal catalyst or if a benzo —NHCbz group is deblocked with a metal catalyst, one potential advantage of performing either transformation in step 6 prior to cyclization in step 7 of Scheme 2 is that less residual metal may bind to the final product II thereby than if cyclization occurred in step 4 prior to the transformation in step 5.

Particular embodiments of the present invention are illustrated by the synthesis of the therapeutically active 3-(4-amino-1-oxoisoindolin-2-yl)-piperidine-2,6-dione in Scheme 3. The description of Scheme 1 and further embodiments described herein for Scheme 1 generally apply to Scheme 3. Specifically, the description of steps 1, 2, 3, 4, 5, 6, and 7 in Scheme 1 and further embodiments described herein for Scheme 1 generally apply to the corresponding steps 1, 2, 3, 4, 5, 6, and 7, respectively, in Scheme 3. Modifications of variables including, but not limited to, reaction solvents, reaction times, reaction temperatures, reagents, starting materials, and functional groups in the particular embodiments of the synthesis of 3-(4-amino-1-oxoisoindolin-2-yl)-piperidine-2, 6-dione will be apparent to those of ordinary skill in the art.

Scheme 3

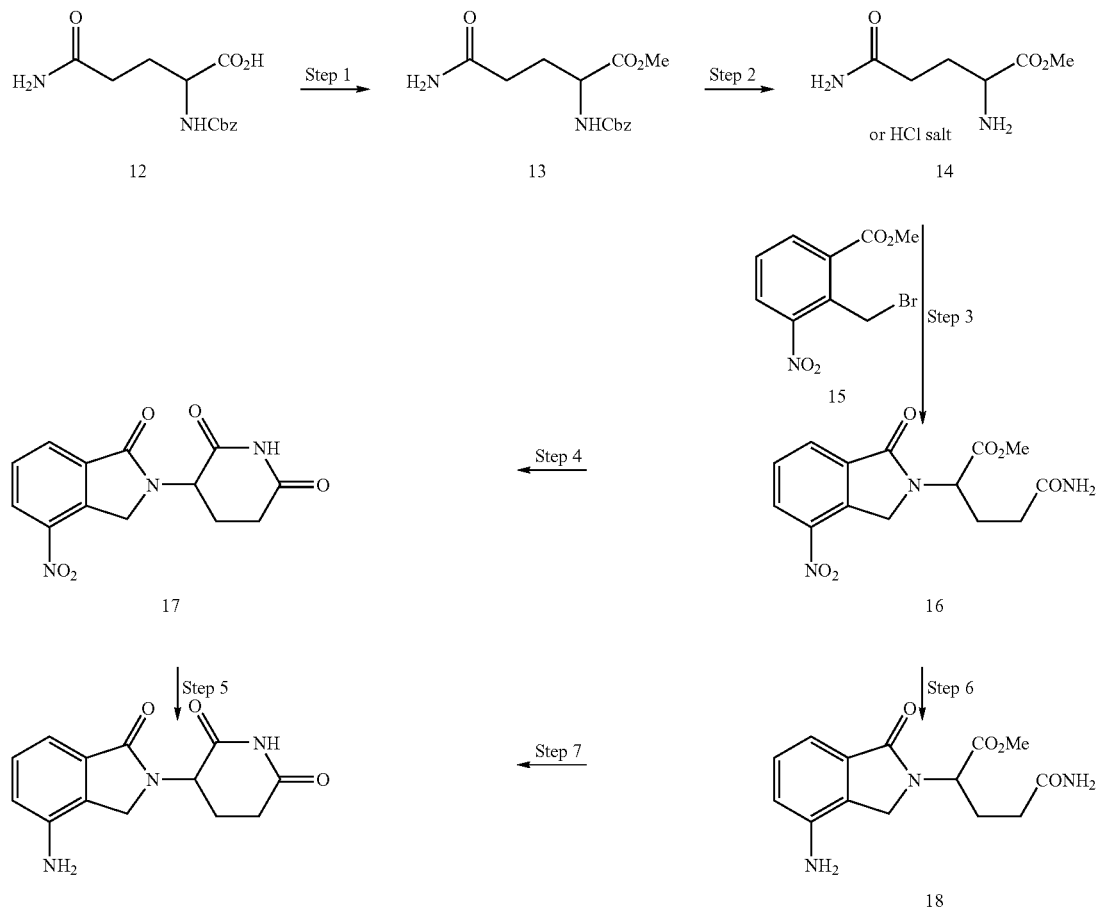

In one embodiment, the invention relates to a process for preparing 3-(4-amino-1-oxoisoindolin-2-yl)-piperidine-2,6-dione:

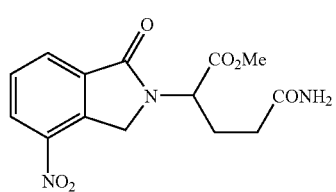

or a pharmaceutically acceptable salt, hydrate, solvate, or polymorph thereof, which comprises the alternative sequences of steps of:

(1)(a) cyclizing a compound of Formula 16:

16

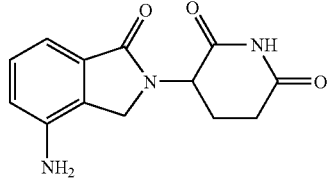

and (b) reducing the —NO₂ group of the cyclized product of Formula 17:

17

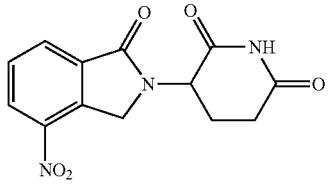

to an —NH₂ group, or:

(2)(a) reducing the —NO₂ group of a compound of Formula 16:

16

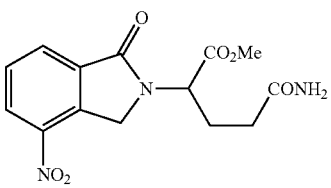

to an —NH₂ group, and
(b) cyclizing the reduced product of Formula 18:

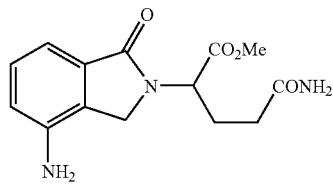

In the particular embodiments of the synthesis of 3-(4-amino-1-oxoisoindolin-2-yl)-piperidine-2,6-dione depicted in Scheme 3, N-Cbz-glutamine 12 (both enantiomers and the racemate are commercially available) is converted to methyl ester 13 with catalytic amounts of acetyl chloride and TMSCl in refluxing methanol. The N-Cbz blocking group is removed by hydrogenolysis over 5% Pd/C in methanol in step 2 to furnish free amine 14. The HCl salts of both enantiomers and the racemate of glutamine methyl ester 14 are also commercially available or can be made directly from the corresponding enantiomer or racemate of glutamine in methanol in the presence of an HCl source, as is well known in the art. The free amine or HCl salt of glutamine methyl ester 14 is then coupled to benzyl bromide 15 in triethylamine/refluxing acetonitrile or NaHCO₃/refluxing acetonitrile to afford oxoisoindoline 16. The synthesis of benzyl bromide 15 is described in International Publication No. WO 98/03502 (See Example 11, page 19).

From common intermediate 16 in Scheme 3, 3-(4-amino-1-oxoisoindolin-2-yl)-piperidine-2,6-dione can be generated in two different ways. Cyclization to form the glutarimide ring can transpire under acidic conditions (e.g., catalytic p-TsOH/refluxing toluene) or basic conditions (e.g., KO′Bu/THF or K₂CO₃/acetonitrile) in step 4 prior to reduction of the nitro group to the final product over 10% Pd/C in methanol in step 5. Alternatively, the nitro group of oxoisoindoline 16 can be reduced to aniline 18 over 5% Pd/C in methanol in step 6, and then cyclization is effected under acidic conditions (e.g., catalytic p-TsOH/refluxing toluene) or basic conditions (e.g., KO′Bu/THF or K₂CO₃/refluxing acetonitrile) to afford the final product in step 7.

The choice of cyclization conditions may be determined by the desired stereochemistry of 3-(4-amino-1-oxoisoindolin-2-yl)-piperidine-2,6-dione. If enantiomerically pure 3-(4-amino-1-oxoisoindolin-2-yl)-piperidine-2,6-dione is desired, cyclization in step 4 or step 7 of Scheme 3 may be conducted under acidic conditions (e.g., catalytic p-TsOH/refluxing toluene) to afford the (S) or (R) final product in a synthesis using L- or D-glutamine methyl ester 14, respectively. On the other hand, if racemic 3-(4-amino-1-oxoisoindolin-2-yl)-piperidine-2,6-dione is desired, cyclization in step 4 or step 7 may be conducted under basic conditions (e.g., KO′Bu/THF or K₂CO₃/acetonitrile) to furnish the racemic final product in a synthesis using less expensive L-glutamine methyl ester hydrochloride 14.

In one embodiment, the processes of the invention are useful for preparing substituted 2-(2,6-dioxopiperidin-3-yl)-1-oxoisoindolines or pharmaceutically acceptable salts, hydrates, solvates, or polymorphs thereof. In another embodiment, the processes of the invention are useful for preparing compounds useful for preventing or treating diseases or conditions related to an abnormally high level or activity of TNFα, including, but not limited to, cancers, inflammatory diseases, and autoimmune diseases.

Polymorphs of 3-(4-amino-1-oxoisoindolin-2-yl)-piperidine-2,6-dione can be prepared according to the methods described in U.S. Provisional Patent Application No. 60/499,723, filed Sep. 4, 2003, which is incorporated herein by reference in its entirety. In one embodiment, Form A of 3-(4-amino-1-oxoisoindolin-2-yl)-piperidine-2,6-dione is an unsolvated, crystalline solid that melts at about 270° C. and is weakly or not hygroscopic. It can be obtained by crystallization from various non-aqueous solvents including, but not limited to, 1-butanol, butyl acetate, ethanol, ethyl acetate, methanol, methyl ethyl ketone, and THF. In another embodiment, Form B of 3-(4-amino-1-oxoisoindolin-2-yl)-piperidine-2,6-dione is a hemihydrated, crystalline solid that melts at about 267° C. It can be obtained by crystallization from various solvents including, but not limited to, hexane, toluene, and water. In yet another embodiment, Form C of 3-(4-amino-1-oxoisoindolin-2-yl)-piperidine-2,6-dione is a hemisolvated, crystalline solid that melts at about 269° C. It can be obtained from evaporations, slurries, and slow cools in solvent systems including, but not limited to, acetone solvent systems. Other polymorphs of 3-(4-amino-1-oxoisoindolin-2-yl)-piperidine-2,6-dione are also obtainable, as described in the above cited patent application.

5. EXAMPLE

Synthesis of Chiral and Racemic 3-(4-amino-1-oxoisoindolin-2-yl)-piperidine-2,6-dione Preparation of L-N-benzyloxycarbonyl-glutamine Methyl Ester (13)

A solution of L-N-Cbz-glutamine, acetyl chloride (0.1 equiv.), and catalytic TMSCl in methanol was refluxed for 4-6 hours, generating the title compound (70-80% yield).

Preparation of L-glutamine Methyl Ester (14)

A mixture of L-N-Cbz-glutamine methyl ester and 5% Pd/C in methanol was stirred under hydrogen (40 psi). The catalyst was filtered and the solvent removed in vacuo. The crude product was used in the ensuing coupling reaction.

Preparation of Methyl N-(1-oxo-4-nitroisoindolin-2-yl)-L-glutamine (16)

To a mixture of L-glutamine methyl ester (0.010 mmol) and methyl 2-bromomethyl-3-nitrobenzoate (0.010 mmol) in acetonitrile (30 mL) was added triethyl amine (0.021 mmol). After the mixture was refluxed for one hour, water (2 mL) was added and acetonitrile was removed in vacuo. Water (50 mL) was added to the resulting residue, giving a solid which was filtered, washed with water, and dried (2.5 g, 56% yield).

Preparation of (S)- or Racemic 3-(4-nitro-1-oxoisoindolin-2-yl)-piperidine-2,6-dione (17) from (S)- or Racemic Methyl N-(1-oxo-4-nitroisoindolin-2-yl)-L-glutamine (A) To a solution of methyl N-(1-oxo-4-nitroisoindolin-2-yl)-L-glutamine (0.2 g, 1.78 mmol) in THF was added 10 mL 0-5° C. KO′Bu under N₂. The solution was stirred for 30 minutes and allowed to warm to room temperature over one hour followed by quenching with water. THF was removed in vacuo. The resulting reside was triturated with CH₂Cl₂/H₂O giving an off-white solid which was filtered, washed with water and dried under reduced pressure (0.45 g, 85% yield).

(B) Alternatively, a mixture of methyl N-(1-oxo-4-nitroisoindolin-2-yl)-L-glutamine (0.2 g, 1.78 mmol) and catalytic p-TsOH in toluene is refluxed for 16 hours and cooled to room temperature. An off-white solid is isolated by filtration and washed with water, 10% NaHCO$_3$ and methanol and dried in vacuo (0.40 g, 91% yield).

Preparation of (S)- or Racemic 3-(4-amino-1-oxoisoindolin-2-yl)-piperidine-2,6-dione from (S)- or Racemic 3-(4-nitro-1-oxoisoindolin-2-yl)-piperidine-2,6-dione, Respectively A mixture of (S)- or racemic 3-(4-nitro-1-oxoisoindolin-2-yl)-piperidine-2,6-dione (1.0 g, 3.5 mmol) and 10% Pd/C (0.3 g) in methanol (600 mL) was hydrogenated in a Parr-Shaker apparatus at 50 psi of hydrogen for 5 hours. The mixture was filtered through Celite and the filtrate was concentrated in vacuo. The solid was slurried in hot ethyl acetate for 30 min, filtered, and dried to afford 0.46 g (51%) of (S) or racemic 3-(4-amino-1-oxoisoindolin-2-yl)-piperidine-2,6-dione, respectively, as a white solid.

Preparation of Methyl N-(1-oxo-4-aminoisoindolin-2-yl)-L-glutamine (18)

A mixture of methyl N-(1-oxo-4-nitroisoindolin-2-yl)-L-glutamine (6.4 g, 0.02 mmol) and 5% Pd/C (0.6 g) in methanol (100 mL) was stirred under hydrogen (40 psi) at ambient temperature for two hours. The Pd catalyst was filtered off through a pad of Celite. After concentration of the filtrate, the resulting oily residue was triturated with MTBE (30 mL), which yielded a solid after standing at ambient temperature for one hour. The off-white solid was filtered, washed with MTBE (30 mL), and dried to furnish the title compound (5.4 g, 93% yield).

Preparation of Racemic 3-(4-amino-1-oxoisoindolin-2-yl)-piperidine-2,6-dione from Methyl N-(1-oxo-4-aminoisoindolin-2-yl)-L-glutamine (A) To a solution of methyl N-(1-oxo-4-aminoisoindolin-2-yl)-L-glutamine in THF at 0° C. was added KO$^t$Bu portionwise. The resulting mixture was stirred at 0-5° C. for 30 minutes, warmed to ambient temperature, and quenched with water (2 mL). THF was removed in vacuo and the resulting residue was triturated with H$_2$O. The resulting off-white solid was filtered, washed with water, and dried. The product had a 4% ee by chiral HPLC and contained 68 ppm of residual Pd.

(B) Alternatively, a solution of methyl N-(1-oxo-4-aminoisoindolin-2-yl)-L-glutamine (0.0295 mmol) and K$_2$CO$_3$ (0.0295 mmol) in acetonitrile (85 mL) was refluxed for one hour. The reaction was then quenched with water (20 mL) and acetonitrile was removed in vacuo, giving an off-white solid. The solid was filtered, washed with water, and dried at ambient temperature for 18 hours to yield the desired compound (65% yield). The solid was slurried in acetonitrile (30 mL) for 15 minutes, filtered, and air-dried for six hours to provide the desired compound that contained less than 1 ppm of residual Pd. The Pd content was determined by inductively coupled plasma (ICP) spectroscopy.

What is claimed is:

1. A process for preparing a compound of Formula 1:

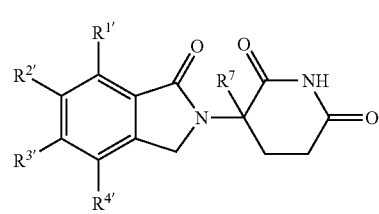

(1)

or a pharmaceutically acceptable salt, thereof, wherein:
each of $R^{1'}$, $R^{2'}$, $R^{3'}$, and $R^{4'}$ is at each occurrence independently hydrogen, halo, alkyl, alkoxy, —CF$_3$, —CN, —NO$_2$, —NHProtG$^2$, or —NR$^5$R$^6$;
each of $R^5$ and $R^6$ is at each occurrence independently hydrogen or alkyl;
$R^7$ is hydrogen, halo, alkyl, or benzyl; and
ProtG$^2$ is a suitable N-protecting group,
which comprises the alternative sequences of steps of:
(1)(a) cyclizing a compound of Formula 2:

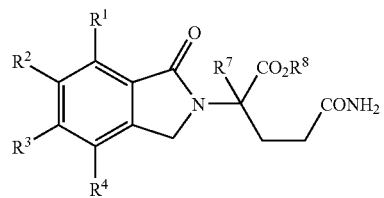

(2)

and
(b) optionally transforming one or more of the $R^1$, $R^2$, $R^3$, and/or $R^4$ substituents of the cyclized product of Formula 3:

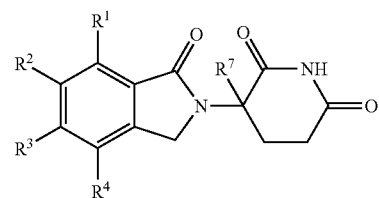

(3)

into one or more of the corresponding $R^{1'}$, $R^{2'}$, $R^{3'}$, and/or $R^{4'}$ substituents, respectively, of the compound of Formula 1 in one or more steps, or:
(2)(a) transforming one or more of the $R^1$, $R^2$, $R^3$, and/or $R^4$ substituents of a compound of Formula 2:

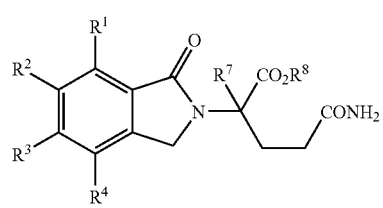

(2)

into one or more of the corresponding $R^{1'}$, $R^{2'}$, $R^{3'}$, and/or $R^{4'}$ substituents, respectively, of a compound of Formula 4:

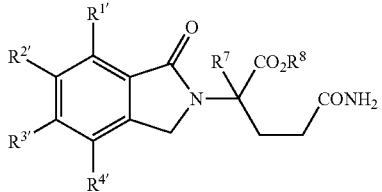

(4)

in one or more steps, and (b) cyclizing the transformed product of Formula 4, wherein, for both sequences of steps unless noted otherwise:
each of $R^1$, $R^2$, $R^3$, $R^4$, $R^{1'}$, $R^{2'}$, $R^{3'}$, and $R^{4'}$ is at each occurrence independently hydrogen, halo, alkyl, alkoxy, —$CF_3$, —CN, —$NO_2$, —$NHProtG^2$, or —$NR^5R^6$;
each of $R^5$ and $R^6$ is at each occurrence independently hydrogen or alkyl;
$R^7$ is hydrogen, halo, alkyl, or benzyl;
$R^8$ is alkyl or benzyl; and
$ProtG^2$ is a suitable N-protecting group,
wherein the cyclizing is performed under acidic condition in an aprotic solvent at a temperature at which the aprotic solvent refluxes or the cyclizing is performed under basic condition in an aprotic solvent at a temperature from about 0 to about 5° C.

2. The process of claim 1, wherein the compound of Formula 1 is racemic.

3. The process of claim 1, wherein the compound of Formula 1 is the (+)- or (−)-enantiomer.

4. The process of claim 1, wherein:
each of $R^1$, $R^2$, $R^3$, and $R^4$ is at each occurrence independently hydrogen, lower molecular weight halo, lower alkyl, lower alkoxy, —$NO_2$, —$NHProtG^2$, or —$NR^5R^6$;
each of $R^{1'}$, $R^{2'}$, $R^{3'}$, and $R^{4'}$ is at each occurrence independently hydrogen, lower molecular weight halo, lower alkyl, lower alkoxy, —$NO_2$, —$NHProtG^2$, or —$NR^5R^6$;
each of $R^5$ and $R^6$ is at each occurrence independently hydrogen or lower alkyl;
$R^7$ is hydrogen or lower alkyl;
$R^8$ is lower alkyl; and
$ProtG^2$ is a suitable acyl N-protecting group.

5. The process of claim 4, wherein:
each of $R^1$, $R^2$, $R^3$, and $R^4$ is at each occurrence independently hydrogen, —$NO_2$, or —$NHProtG^2$;
each of $R^{1'}$, $R^{2'}$, $R^{3'}$, and $R^{4'}$ is at each occurrence independently hydrogen, —$NHProtG^2$, or —$NH_2$;
$R^7$ is hydrogen or methyl;
$R^8$ is methyl; and
$ProtG^2$ is Cbz, Boc, formyl, acetyl, trifluoroacetyl, or pivaloyl.

6. The process of claim 1, wherein the cyclizing occurs in the presence of p-toluenesulfonic acid.

7. The process of claim 1, wherein the cyclizing occurs in the presence of KO$^t$Bu.

8. The process of claim 1, wherein the cyclizing occurs in the presence of $K_2CO_3$.

9. The process of claim 1, wherein the transforming one or more of the $R^1$, $R^2$, $R^3$, and/or $R^4$ substituents of the compound of Formula 2 or 3 into one or more of the corresponding $R^{1'}$, $R^{2'}$, $R^{3'}$, and/or $R^{4'}$ substituents, respectively, of the compound of Formula 4 or 1, respectively, comprises reducing one or more benzo —$NO_2$ groups to one or more benzo —$NH_2$ groups.

10. The process of claim 9, wherein the reducing is facilitated by a catalyst.

11. The process of claim 10, wherein the metal catalyst is a Pd catalyst.

12. The process of claim 1, wherein the transforming one or more of the $R^1$, $R^2$, $R^3$, and/or $R^4$ substituents of the compound of Formula 2 or 3 into one or more of the corresponding $R^{1'}$, $R^{2'}$, $R^{3'}$, and/or $R^{4'}$ substituents, respectively, of the compound of Formula 4 or 1, respectively, in one or more steps comprises deprotecting one or more benzo —$NHProtG^2$ groups to yield one or more benzo —$NH_2$ groups in one or more steps.

13. The process of claim 12, wherein the deprotecting cleaves one or more benzo —NHCbz groups by hydrogenolysis with a catalyst to yield one or more benzo —$NH_2$ groups.

14. The process of claim 12, wherein the deprotecting cleaves one or more benzo —NHBoc groups under acidic condition to give one or more benzo —$NH_2$ groups.

15. The process of claim 1, wherein the compound of Formula 2 is prepared by coupling the α-amino group of a compound of Formula 5:

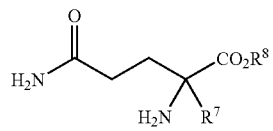

(5)

or a salt thereof, wherein:
$R^7$ is hydrogen, halo, alkyl, or benzyl, and
$R^8$ is alkyl or benzyl,
with the $CO_2R^9$ group a compound of Formula 6:

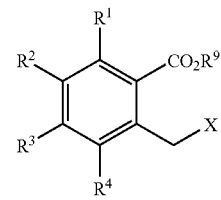

(6)

wherein:
each of $R^1$, $R^2$, $R^3$, and $R^4$ is at each occurrence independently hydrogen, halo, alkyl, alkoxy, —$CF_3$, —CN, —$NO_2$, —$NHProtG^2$, or —$NR^5R^6$;
each of $R^5$ and $R^6$ is at each occurrence independently hydrogen or alkyl;
$R^9$ is alkyl;
X is halo; and
$ProtG^2$ is a suitable N-protecting group.

16. The process of claim 15, wherein:
each of $R^1$, $R^2$, $R^3$, and $R^4$ is at each occurrence independently hydrogen, lower molecular weight halo, lower alkyl, lower alkoxy, —$NO_2$, —$NHProtG^2$, or —$NR^5R^6$;
each of $R^5$ and $R^6$ is at each occurrence independently hydrogen or lower alkyl;
$R^7$ is hydrogen or lower alkyl;
$R^8$ is lower alkyl or benzyl;
$R^9$ is lower alkyl;

X is higher molecular weight halo; and

ProtG² is a suitable acyl N-protecting group.

17. The process of claim 16, wherein:

each of $R^1$, $R^2$, $R^3$, and $R^4$ is at each occurrence independently hydrogen, —$NO_2$, or —NHProtG²;

$R^7$ is hydrogen or methyl;

$R^8$ is methyl;

$R^9$ is methyl;

X is bromo; and

ProtG² is Cbz, Boc, formyl, acetyl, trifluoroacetyl, or pivaloyl.

18. The process of claim 16, wherein the coupling occurs under basic condition.

19. The process of claim 18, wherein the coupling occurs in the presence of $NEt_3$.

20. The process of claim 18, wherein the coupling occurs in the presence of $iPrEt_2N$.

21. The process of claim 18, wherein the coupling occurs in the presence of $NaHCO_3$.

22. The process of claim 15, wherein the compound of Formula 5 or a salt thereof is prepared by esterifying a compound of Formula 7:

$$\underset{H_2N}{\overset{O}{\|}}\diagdown\diagup\diagdown\underset{H_2N}{\overset{}{\underset{R^7}{|}}}CO_2H \qquad (7)$$

or a salt thereof, wherein $R^7$ is hydrogen, halo, alkyl, or benzyl.

23. The process of claim 22, wherein the esterifying occurs under acidic condition in an alcohol of the formula of $R^8OH$.

24. The process of claim 15, wherein the compound of Formula 5 or a salt thereof is prepared by:

protecting the α-amino group of a compound of Formula 7:

$$\underset{H_2N}{\overset{O}{\|}}\diagdown\diagup\diagdown\underset{H_2N}{\overset{}{\underset{R^7}{|}}}CO_2H \qquad (7)$$

or a salt thereof;

esterifying the N-protected compound of Formula 8:

$$\underset{H_2N}{\overset{O}{\|}}\diagdown\diagup\diagdown\underset{PG^1HN}{\overset{}{\underset{R^7}{|}}}CO_2H \qquad (8)$$

and deprotecting the α-amino group of the esterified compound of Formula 9:

$$\underset{H_2N}{\overset{O}{\|}}\diagdown\diagup\diagdown\underset{PG^1HN}{\overset{}{\underset{R^7}{|}}}CO_2R^8 \qquad (9)$$

wherein:

$R^7$ is hydrogen, halo, alkyl, or benzyl;

$R^8$ is alkyl or benzyl; and

ProtG¹ is a suitable N-protecting group.

25. The process of claim 24, wherein the esterifying occurs under acidic condition in an alcohol of the formula of $R^8OH$.

26. The process of claim 24, wherein the deprotecting comprises removing a Cbz group by hydrogenolysis with a catalyst.

27. The process of claim 15, wherein the compound of Formula 6 is prepared by halogenating a compound of Formula 10:

$$(10)$$

wherein:

each of $R^1$, $R^2$, $R^3$, and $R^4$ is at each occurrence independently hydrogen, halo, alkyl, alkoxy, —$CF_3$, —CN, —$NO_2$, —NHProtG², or —$NR^5R^6$;

each of $R^5$ and $R^6$ is at each occurrence independently hydrogen or alkyl;

$R^9$ is alkyl; and

ProtG² is a suitable N-protecting group.

28. The process of claim 27, wherein the halogenating comprises brominating with a brominating agent under free-radical condition.

29. A process for preparing a compound of Formula 11:

$$(11)$$

or a pharmaceutically acceptable salt thereof, which comprises the alternative sequences of steps of:

(1)(a) cyclizing a compound of Formula 12:

(12)

[Structure of Formula 12: isoindolinone with NO₂ group, N-substituted with CH(CO₂Me)CH₂CH₂CONH₂]

and
(b) reducing the —NO₂ group of the cyclized product of Formula 13:

(13)

[Structure of Formula 13: isoindolinone with NO₂ group, N-substituted with glutarimide ring]

to an —NH₂ group,
or:
(2)(a) reducing the —NO₂ group of a compound of Formula 12:

(12)

[Structure of Formula 12]

to an —NH₂ group, and
(b) cyclizing the reduced product of Formula 14:

(14)

[Structure of Formula 14: isoindolinone with NH₂ group, N-substituted with CH(CO₂Me)CH₂CH₂CONH₂]

wherein the cyclizing is performed under acidic condition in an aprotic solvent at a temperature at which the aprotic solvent refluxes or the cyclizing is performed under basic condition in an aprotic solvent at a temperature from about 0 to about 5° C.

30. The process of claim 29, wherein the compound of Formula 11 is racemic.

31. The process of claim 29, wherein the compound of Formula 11 is the (+)- or (−)-enantiomer.

32. The process of claim 29, wherein the cyclizing occurs in the presence of p-toluenesulfonic acid.

33. The process of claim 29, wherein the cyclizing occurs in the presence of KO$^t$Bu.

34. The process of claim 29, wherein the cyclizing occurs in the presence of $K_2CO_3$.

35. The process of claim 29, wherein the reducing is facilitated by a catalyst.

36. The process of claim 35, wherein the catalyst is a Pd catalyst.

37. The process of claim 29, wherein the compound of Formula 12 is prepared by coupling a compound of Formula 15:

(15)

[Structure of Formula 15: H₂N-C(=O)-CH₂CH₂-CH(NH₂)-CO₂Me]

or a salt thereof with a compound of Formula 16:

(16)

[Structure of Formula 16: benzene with CO₂Me, CH₂Br, and NO₂ substituents]

38. The process of claim 37, wherein the coupling occurs under basic condition.

39. The process of claim 38, wherein the coupling occurs in the presence of $NEt_3$.

40. The process of claim 38, wherein the coupling occurs in the presence of $NaHCO_3$.

41. The process of claim 37, wherein the compound of Formula 15 or a salt thereof is prepared by esterifying a compound of Formula 17:

(17)

[Structure of Formula 17: H₂N-C(=O)-CH₂CH₂-CH(NH₂)-CO₂H]

or a salt thereof as a methyl ester.

42. The process of claim 41, wherein the esterifying occurs in methanol under acidic condition.

43. The process of claim 37, wherein the compound of Formula 15 or a salt thereof is prepared by:
protecting the α-amino group of a compound of Formula 17:

(17)

[Structure of Formula 17]

or a salt thereof as a benzyloxycarbonyl carbamate;

esterifying the N-protected compound of Formula 18:

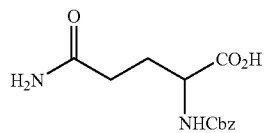
(18)

as a methyl ester; and deprotecting the α-amino group of the esterified compound of Formula 19:

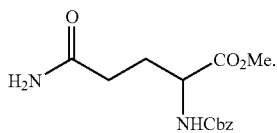
(19)

44. The process of claim 43, wherein the esterifying occurs in methanol under acidic condition.

45. The process of claim 43, wherein the deprotecting comprises removing the benzyloxycarbonyl group by hydrogenolysis with a catalyst.

46. The process of claim 45, wherein the catalyst is a Pd catalyst.

47. The process of claim 37, wherein the compound of Formula 16 is prepared by brominating a compound of Formula 20:

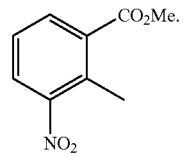
(20)

48. The process of claim 47, wherein the brominating is effected by a brominating agent in the presence of a free-radical initiator.

49. The process of claim 48, wherein the brominating agent is N-bromosuccinimide.

50. The process of claim 48, wherein the free radical initiator is light.

51. The process of claim 48, wherein the free radical initiator is 1,1'-azobis-(cyclohexanecarbonitrile).

52. The process of claim 1, wherein the aprotic solvent is polar.

53. The process of claim 1, wherein the aprotic solvent is toluene, tetrahydrofuran or acetonitrile.

54. The process of claim 29, wherein the aprotic solvent is polar.

55. The process of claim 29, wherein the aprotic solvent is toluene, tetrahydrofuran or acetonitrile.

* * * * *